(12) United States Patent
Peleg et al.

(10) Patent No.: US 11,779,463 B2
(45) Date of Patent: Oct. 10, 2023

(54) CONTRACTION OF AN ANNULOPLASTY STRUCTURE

(71) Applicant: Edwards Lifesciences Innovation (Israel) Ltd., Caesarea (IL)

(72) Inventors: Carmel Peleg, Neve Monoson (IL); Yehuda Cohen, Petah Tikva (IL); Haim Brauon, Beit Dagan (IL); Yuval Zipory, Modi'in (IL)

(73) Assignee: Edwards Lifesciences Innovation (Israel) Ltd., Caesarea (IL)

( * ) Notice: Subject to any disclaimer, the term of this patent is extended or adjusted under 35 U.S.C. 154(b) by 668 days.

(21) Appl. No.: 16/889,621

(22) Filed: Jun. 1, 2020

(65) Prior Publication Data

US 2020/0289267 A1    Sep. 17, 2020

Related U.S. Application Data

(63) Continuation of application No. PCT/IL2019/050092, filed on Jan. 23, 2019.

(60) Provisional application No. 62/621,280, filed on Jan. 24, 2018.

(51) Int. Cl.
*A61F 2/24* (2006.01)

(52) U.S. Cl.
CPC .......... *A61F 2/2466* (2013.01); *A61F 2/2442* (2013.01); *A61F 2/2445* (2013.01); *A61F 2220/0075* (2013.01)

(58) Field of Classification Search
CPC ..... A61F 2/2442; A61F 2/2445; A61F 2/2466
See application file for complete search history.

(56) References Cited

U.S. PATENT DOCUMENTS

| | | |
|---|---|---|
| 3,604,488 A | 9/1971 | Wishart et al. |
| 3,656,185 A | 4/1972 | Carpentier |
| 3,840,018 A | 10/1974 | Heifetz |
| 3,881,366 A | 5/1975 | Bradley et al. |

(Continued)

FOREIGN PATENT DOCUMENTS

| | | |
|---|---|---|
| CN | 113331995 A | 9/2021 |
| EP | 1034753 A1 | 9/2000 |

(Continued)

OTHER PUBLICATIONS

Agarwal et al. International Cardiology Perspective Functional Tricuspid Regurgitation, Circ Cardiovasc Interv 2009;2;2;565-573 (2009).

(Continued)

*Primary Examiner* — William H Matthews
(74) *Attorney, Agent, or Firm* — Thomas C. Richardson

(57) ABSTRACT

An annuloplasty structure includes a flexible sleeve and an elongate contraction wire. The sleeve has a first sleeve-end-portion, a second sleeve-end-portion, and a circumferential wall that defines a longitudinal lumen between the first and second sleeve-end-portions. The contraction wire has a first wire-end and a second wire-end, the first wire-end being attached to the sleeve at the first sleeve-end-portion. The wire extends, in association with the circumferential wall, from the first sleeve-end-portion to the second sleeve-end-portion. The wire is arranged with respect to the sleeve such that increasing a longitudinal proportion of the wire that is disposed within the lumen longitudinally contracts the sleeve. Other embodiments are also provided.

15 Claims, 14 Drawing Sheets

(56) References Cited

U.S. PATENT DOCUMENTS

| | | |
|---|---|---|
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,752,963 A | 5/1998 | Allard et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 5,993,459 A | 11/1999 | Larsen et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |

(56) References Cited

U.S. PATENT DOCUMENTS

| | | |
|---|---|---|
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego |
| 7,955,315 B2 | 6/2011 | Feinberg et al. |
| 7,955,377 B2 | 6/2011 | Meisheimer |
| 7,981,152 B1 | 7/2011 | Webler et al. |
| 7,992,567 B2 | 8/2011 | Hiratsuka et al. |
| 7,993,368 B2 | 8/2011 | Gambale et al. |
| 7,993,397 B2 | 8/2011 | Lashinski |
| 8,012,201 B2 | 9/2011 | Lashinski |
| 8,034,103 B2 | 10/2011 | Burriesci et al. |
| 8,052,592 B2 | 11/2011 | Goldfarb et al. |
| 8,057,493 B2 | 11/2011 | Goldfarb |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |

(56) References Cited

U.S. PATENT DOCUMENTS

| | | |
|---|---|---|
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0083538 A1 | 5/2003 | Adams et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0002735 A1 | 1/2004 | Lizardi et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |

(56) References Cited

U.S. PATENT DOCUMENTS

| | | |
|---|---|---|
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1 | 10/2005 | Martinek et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1 | 10/2007 | Rafiee et al. |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1 | 9/2008 | Godin |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |

(56) References Cited

U.S. PATENT DOCUMENTS

| | | |
|---|---|---|
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144576 A1 | 6/2011 | Rothe et al. |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0053628 A1 | 3/2012 | Sojka et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |

(56) References Cited

U.S. PATENT DOCUMENTS

| | | |
|---|---|---|
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0029920 A1 | 2/2016 | Kronstrom et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0100119 A1 | 4/2017 | Baird et al. |
| 2017/0224489 A1 | 8/2017 | Starksen et al. |
| 2017/0245993 A1 | 8/2017 | Gross et al. |
| 2018/0008907 A1 | 1/2018 | Kutzik et al. |
| 2018/0049875 A1 | 2/2018 | Iflah et al. |
| 2018/0140420 A1 | 5/2018 | Hayoz et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0159898 A1 | 5/2019 | Kutzik et al. |
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0240023 A1 | 8/2019 | Spence et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015971 A1 | 1/2020 | Brauon et al. |
| 2020/0289267 A1 | 9/2020 | Peleg et al. |
| 2020/0337840 A1 | 10/2020 | Reich |
| 2021/0015475 A1 | 1/2021 | Lau |
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2021/0145584 A1 | 5/2021 | Kasher et al. |
| 2022/0071620 A1 | 3/2022 | Brauon et al. |
| 2022/0096232 A1 | 3/2022 | Skaro et al. |
| 2022/0142779 A1 | 5/2022 | Sharon |
| 2022/0176076 A1 | 6/2022 | Keidar |
| 2022/0233316 A1 | 7/2022 | Sheps et al. |
| 2022/0273436 A1 | 9/2022 | Aviv et al. |
| 2022/0313438 A1 | 10/2022 | Chappel-Ram |
| 2022/0323221 A1 | 10/2022 | Sharon et al. |
| 2023/0016867 A1 | 1/2023 | Tennenbaum |

FOREIGN PATENT DOCUMENTS

| | | |
|---|---|---|
| EP | 3531975 A1 | 9/2019 |
| WO | 9205093 A1 | 4/1992 |
| WO | 9846149 A1 | 10/1998 |
| WO | 02085250 A3 | 2/2003 |
| WO | 03047467 A1 | 6/2003 |
| WO | 2007098512 A1 | 9/2007 |
| WO | 2010000454 A1 | 1/2010 |
| WO | 2012063228 A1 | 5/2012 |
| WO | 2012176195 A3 | 3/2013 |
| WO | 2014064964 A1 | 5/2014 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |
| WO | 2020240282 A2 | 12/2020 |
| WO | 2021014440 A2 | 1/2021 |
| WO | 2021038559 A1 | 3/2021 |
| WO | 2021038560 A1 | 3/2021 |
| WO | 2022064401 A2 | 3/2022 |
| WO | 2022090907 A1 | 5/2022 |
| WO | 2022101817 A2 | 5/2022 |
| WO | 2022153131 A1 | 7/2022 |
| WO | 2022157592 A1 | 7/2022 |
| WO | 2022172108 A1 | 8/2022 |
| WO | 2022172149 A1 | 8/2022 |
| WO | 2022200972 A1 | 9/2022 |
| WO | 2022224071 A1 | 10/2022 |
| WO | 2022229815 A1 | 11/2022 |
| WO | 2022250983 A1 | 12/2022 |

OTHER PUBLICATIONS

Ahmadi, A., G. Spillner, and Th Johannessen. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneousiy adjustable pulmonary artery band." The Annals of thoracic surgery 60 (1995): S520-S522.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri et al."Novel Suture Device for Beating-Heart Mitral Leaflet Approximation", Ann Thorac Surg. 2002, 74:1488-1493.

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

Amplatzer® Cribriform Occluder. A patient guide to Percutaneous, Transcatheter, Atrial Septal Defect Closuer, AGA Medical Corporation, Apr. 2008.

(56) References Cited

OTHER PUBLICATIONS

Amplatzer® Septal Occluder. A patient guide to the Non-Surgical Closuer of the Atrial Septal Defect Using the Amplatzer Septal Occluder System, AGA Medical Corporation, Apr. 2008.
Assad, Renato S. "Adjustable Pulmonary Artery Banding." (2014).
Brennan, Jennifer, 510(k) Summary of safety and effectiveness, Jan. 2008.
Daebritz, S. et al. "Experience with an adjustable pulmonary artery banding device in two cases: initial success-midterm failure." The Thoracic and cardiovascular surgeon 47.01 (1999): 51-52.
Dang NC et al. "Simplified Placement of Multiple Artificial Mitral Valve Chords," The Heart Surgery Forum #2005-1005, 8 (3) (2005).
Dictionary.com definition of "lock", Jul. 29, 2013.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
Elliott, Daniel S., Gerald W. Timm, and David M. Barrett. "An implantable mechanical urinary sphincter: a new nonhydraulic design concept." Urology 52.6 (1998): 1151-1154.
Langer et al. Ring plus String: Papillary muscle repositioning as an adjunctive repair technique for ischemic mitral regurgitation, The Journal of Thoracic Cardiovascular surgery vol. 133 No. 1, Jan. 2007.
Langer et al. Ring+String, Successful Repair technique for ischemic mitral regurgitation with severe leaflet Tethering, The Department of Thoracic Cardiovascular surgery, Hamburg, Germany, Nov. 2008.
Maisano, "The double-orifice technique as a standardized approach to treat mitral," European Journal of Cardio-thoracic Surgery 17 (2000) 201-205.
Odell JA et al., "Early Results o4yf a Simplified Method of Mitral Valve Annuloplasty," Circulation 92:150-154 (1995).
O'Reilly S et al., "Heart valve surgery pushes the envelope," Medtech insight 8(3): 73, 99-108 (2006).
Park, Sang C. et al. "A percutaneousiy adjustable device for banding of the pulmonary trunk." International journal of cardiology 9.4 (1985): 477-484.
Swain CP et al., "An endoscopically deliverable tissue-transfixing device for securing biosensors in the gastrointestinal tract," Gastrointestinal Endoscopy 40(6): 730-734 (1994).
Swenson, O. An experimental implantable urinary sphincter. Invest Urol. Sep. 1976;14(2):100-3.
Swenson, O. and Malinin, T.I., 1978. An improved mechanical device for control of urinary incontinence. Investigative urology, 15(5), pp. 389-391.
Swenson, Orvar. "Internal device for control of urinary incontinence." Journal of pediatric surgery 7.5 (1972): 542-545.
Tajik, Abdul, "Two dimensional real-time ultrasonic imaging of the heart and great vessels", Mayo Clin Proc. vol. 53:271-303, 1978.

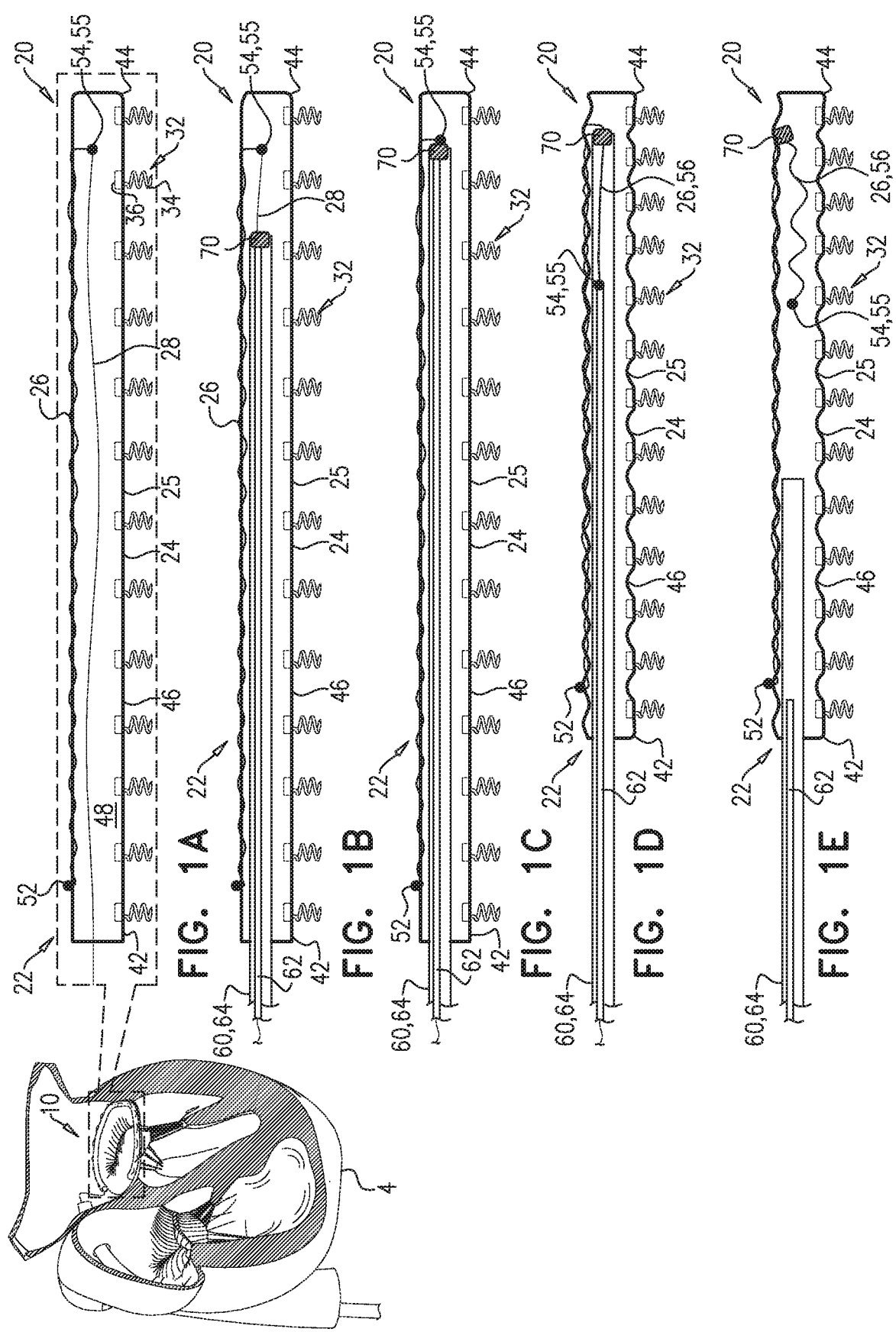

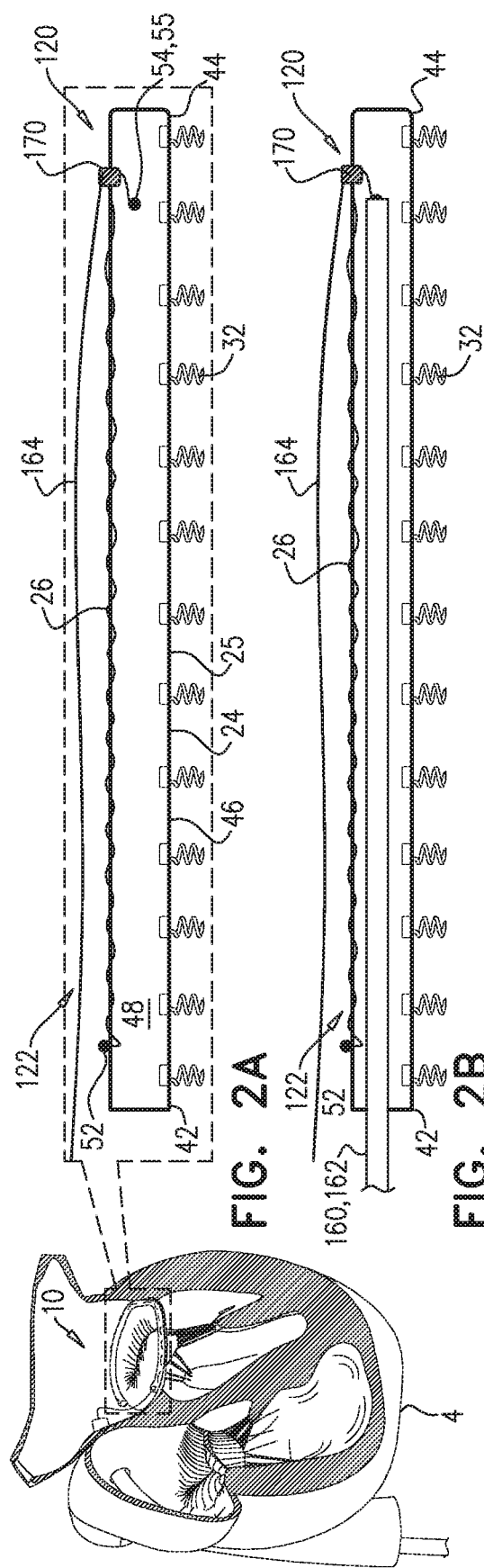

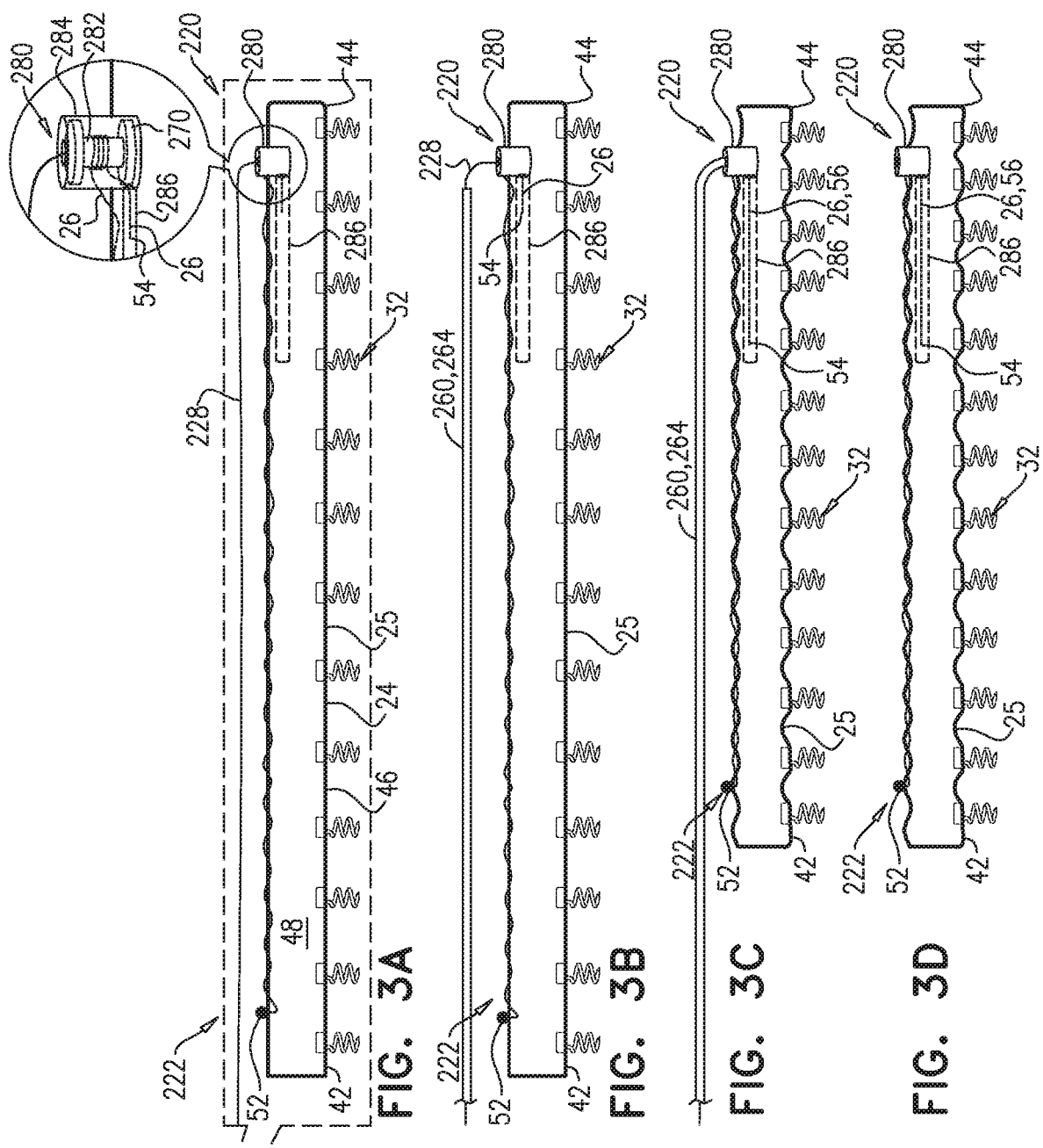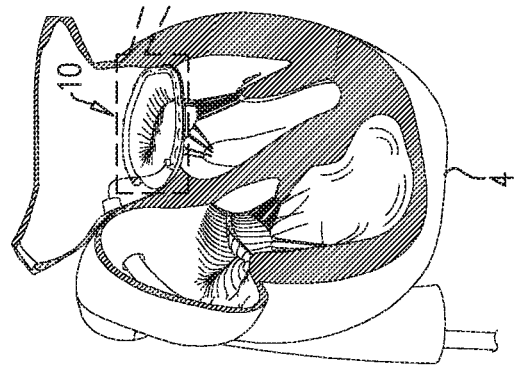

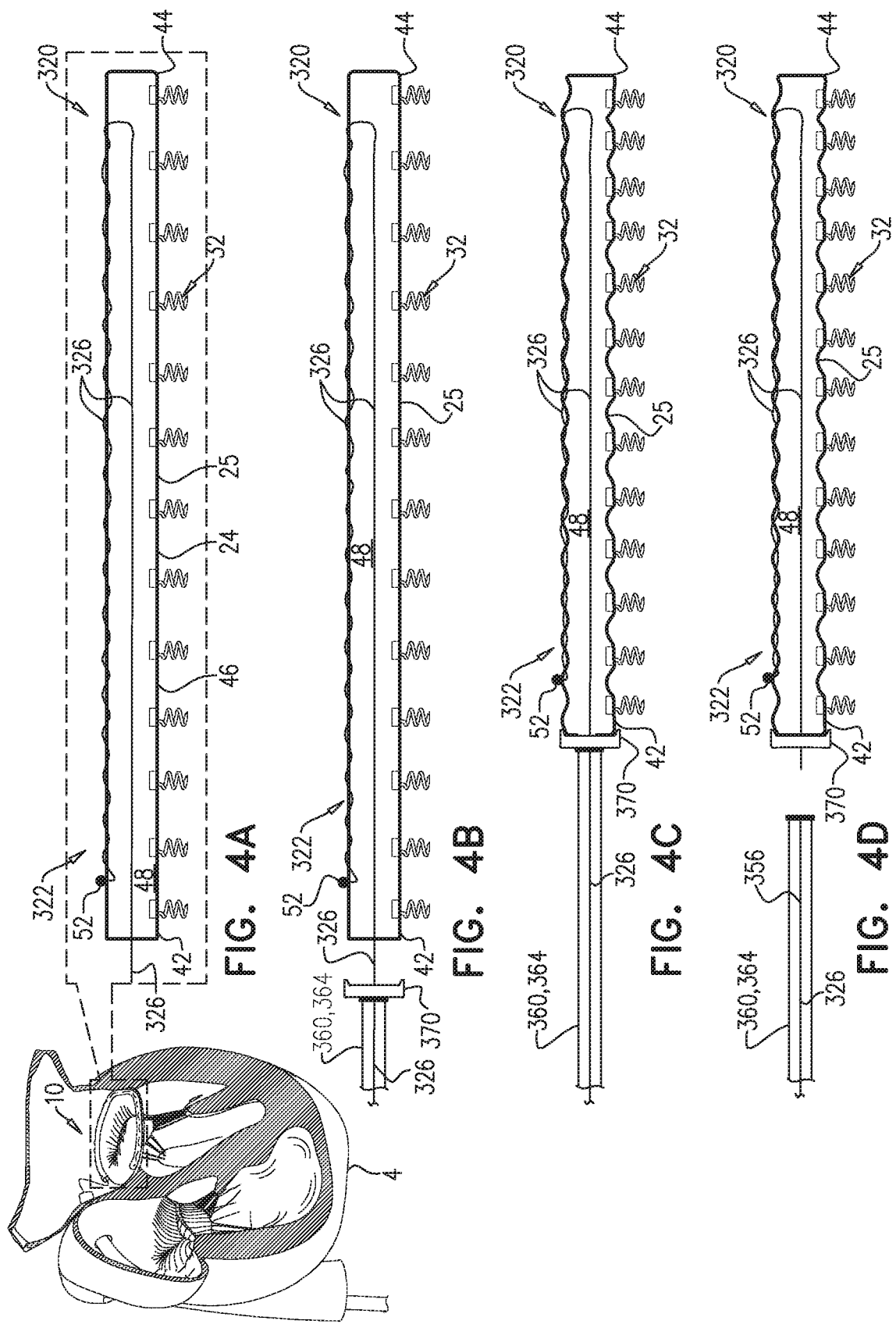

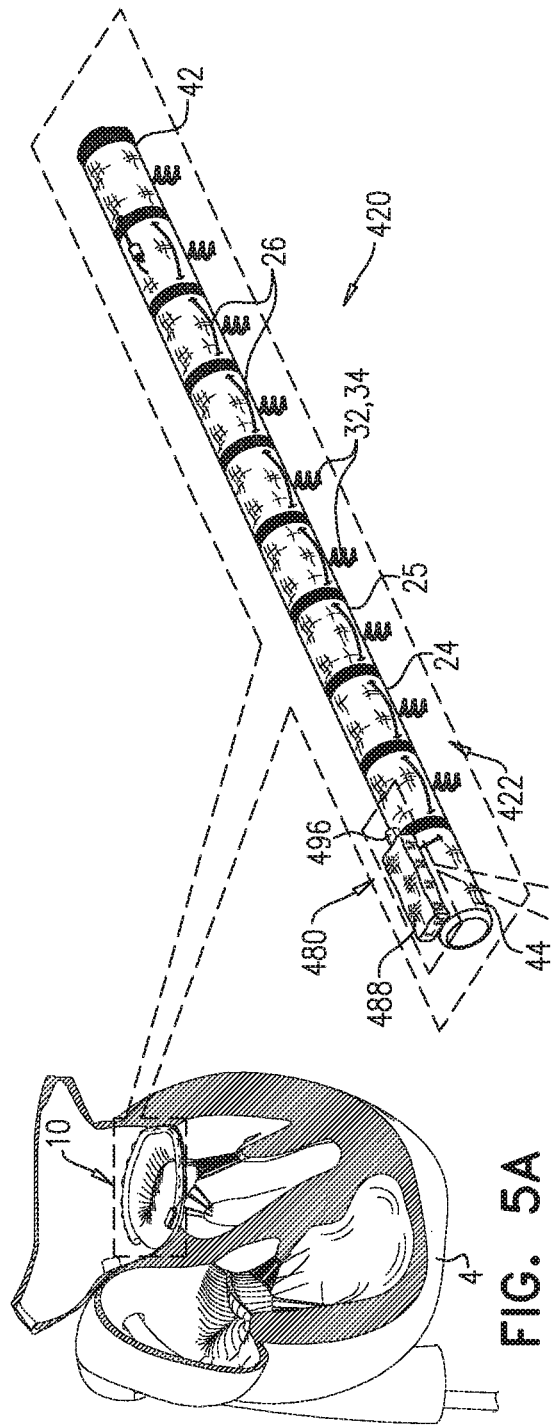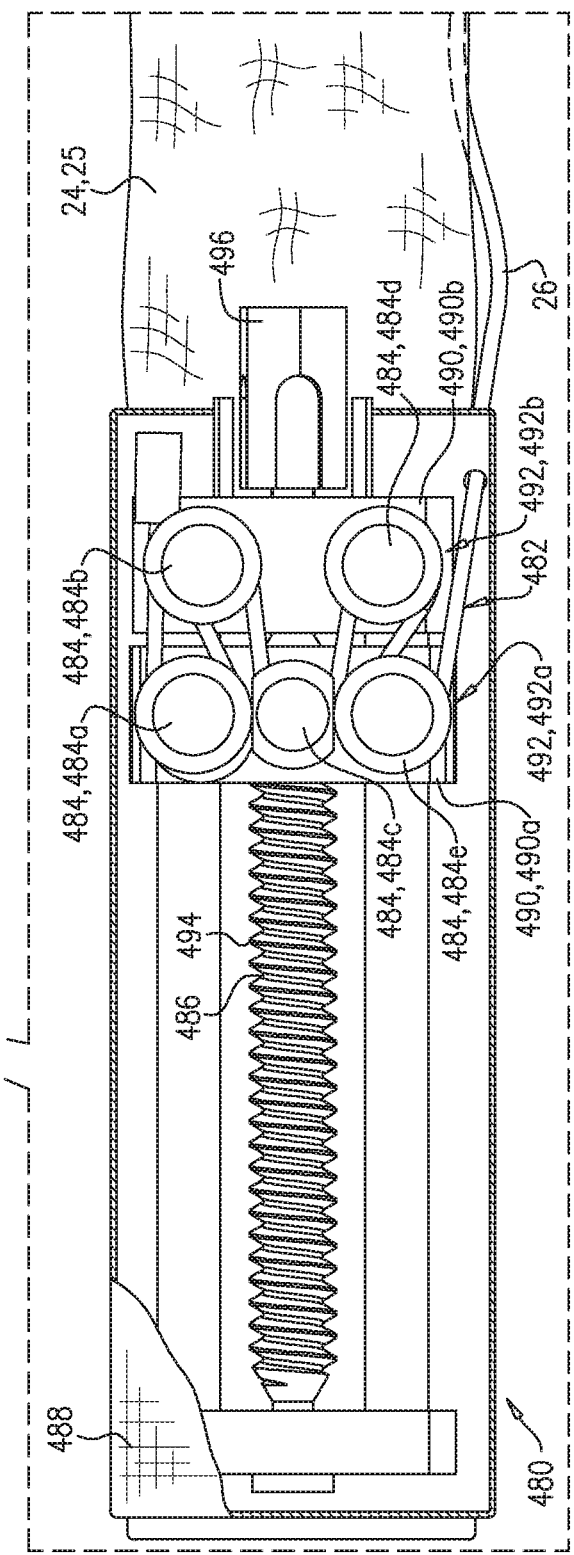
FIG. 5A

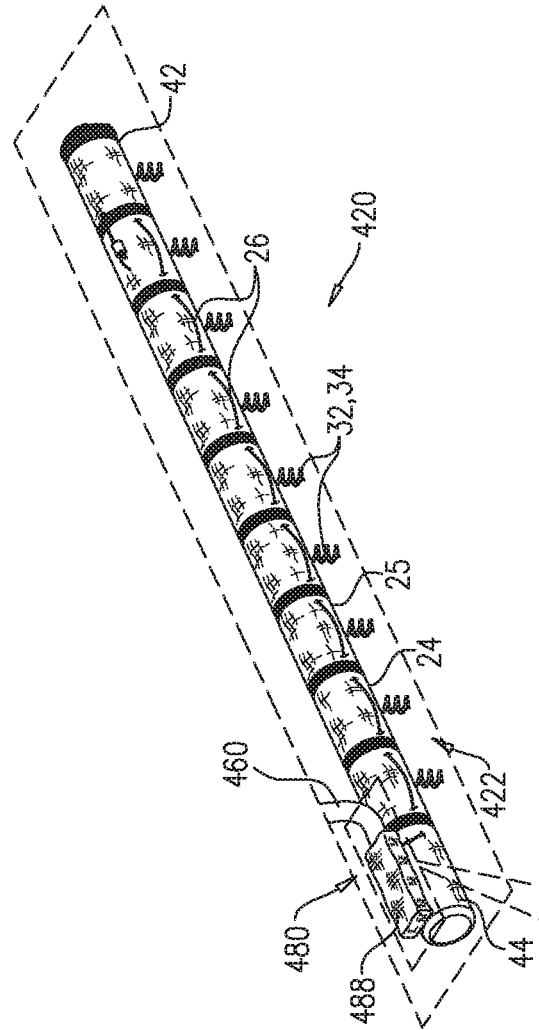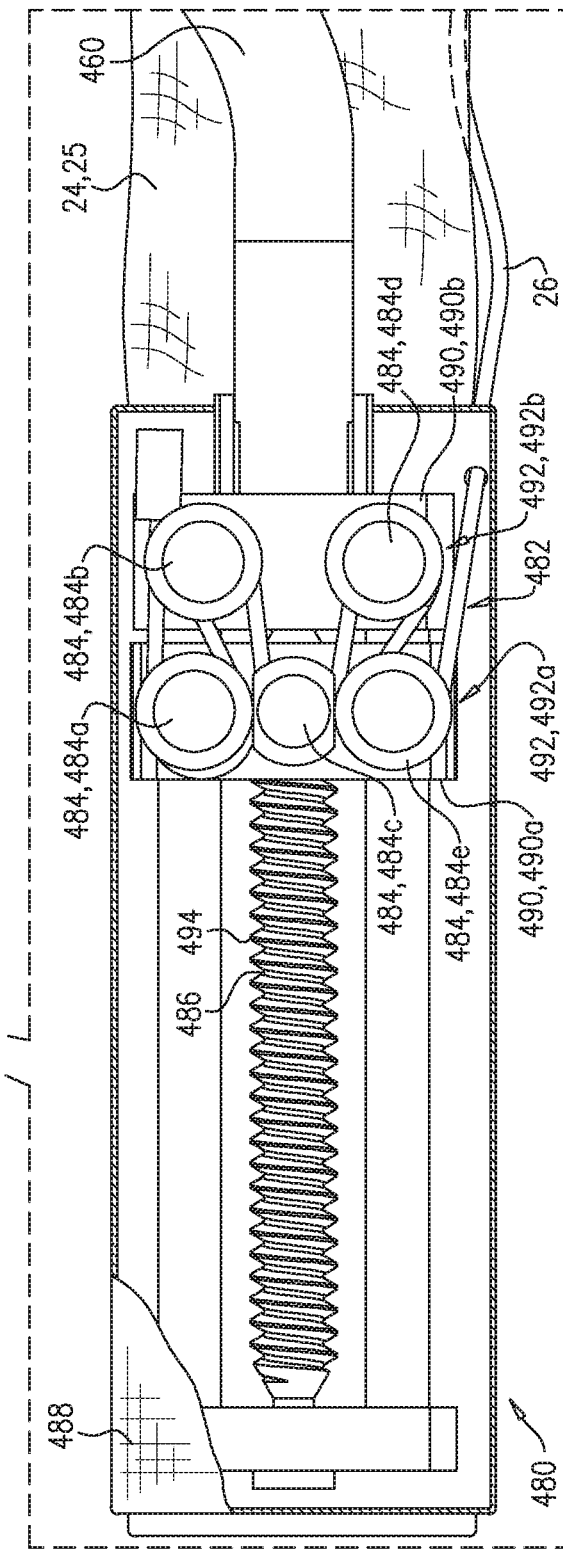
FIG. 5B

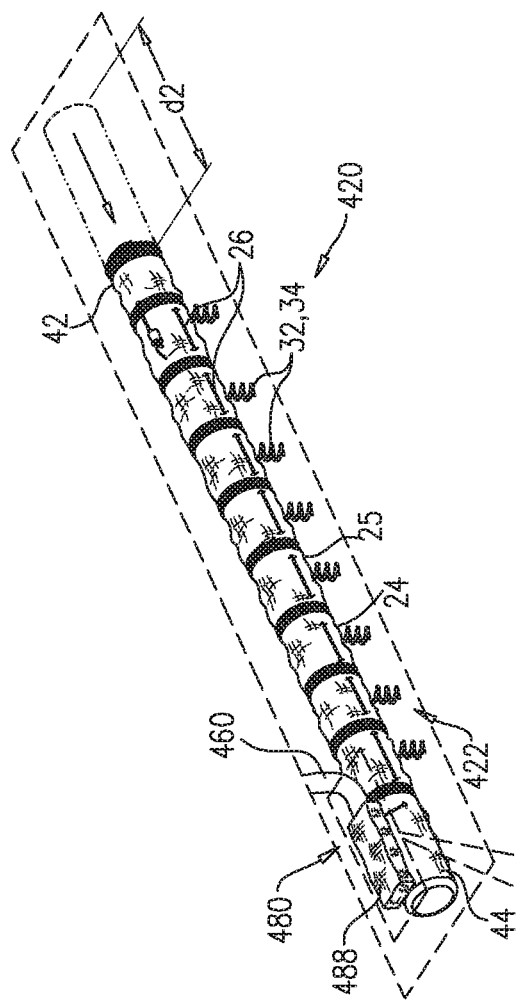
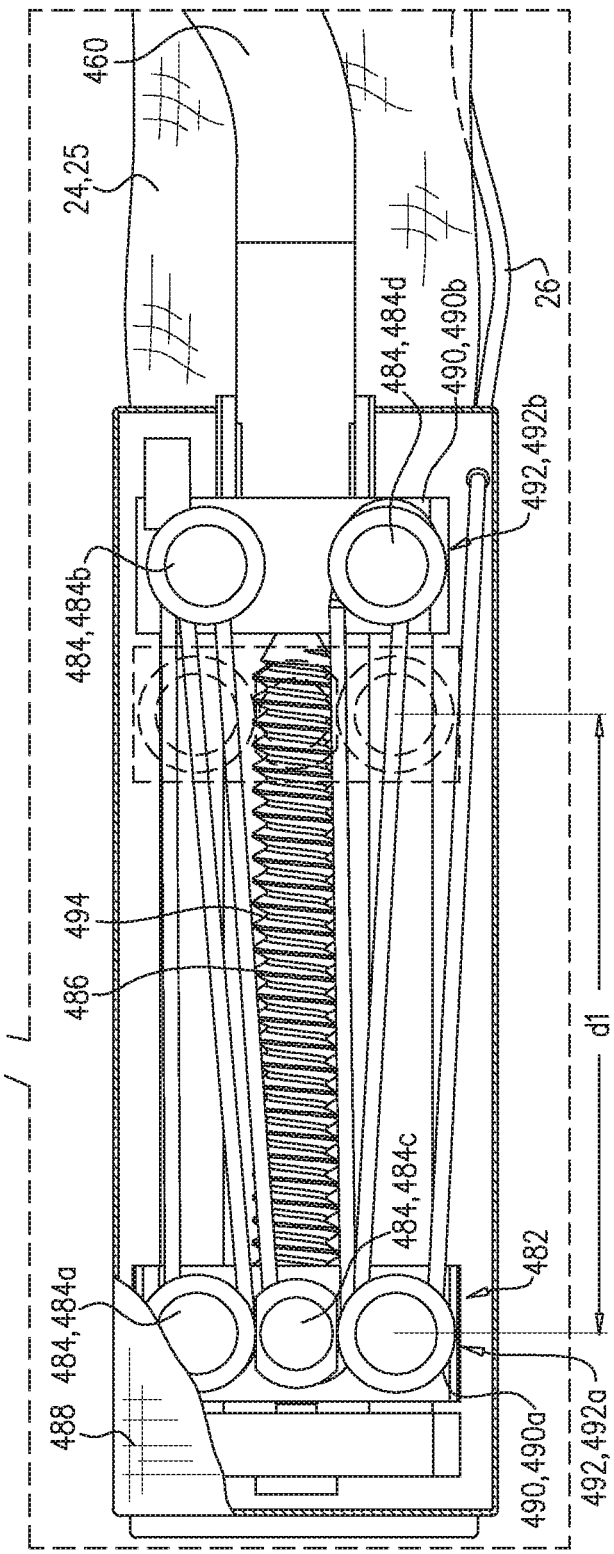
FIG. 5C

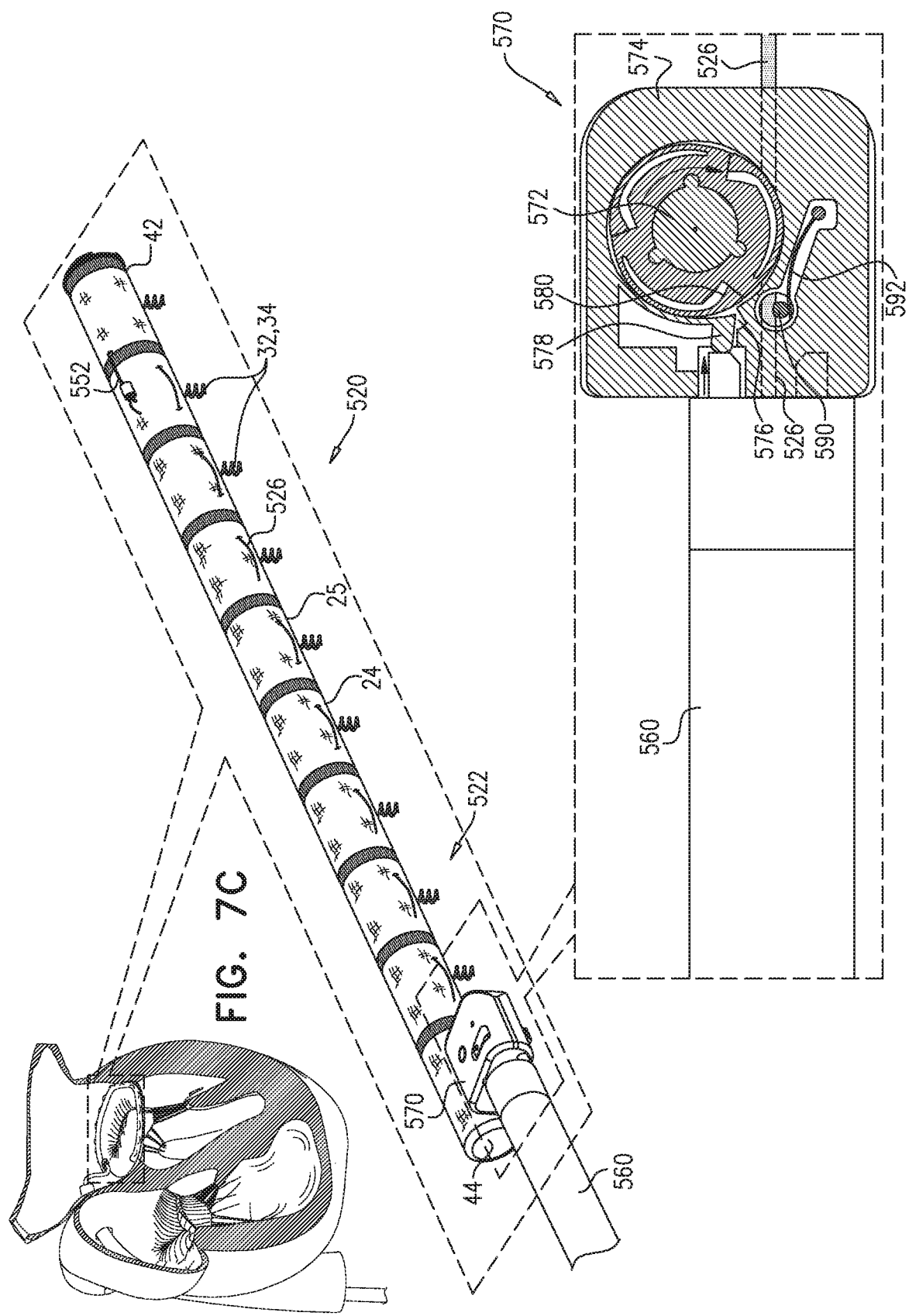

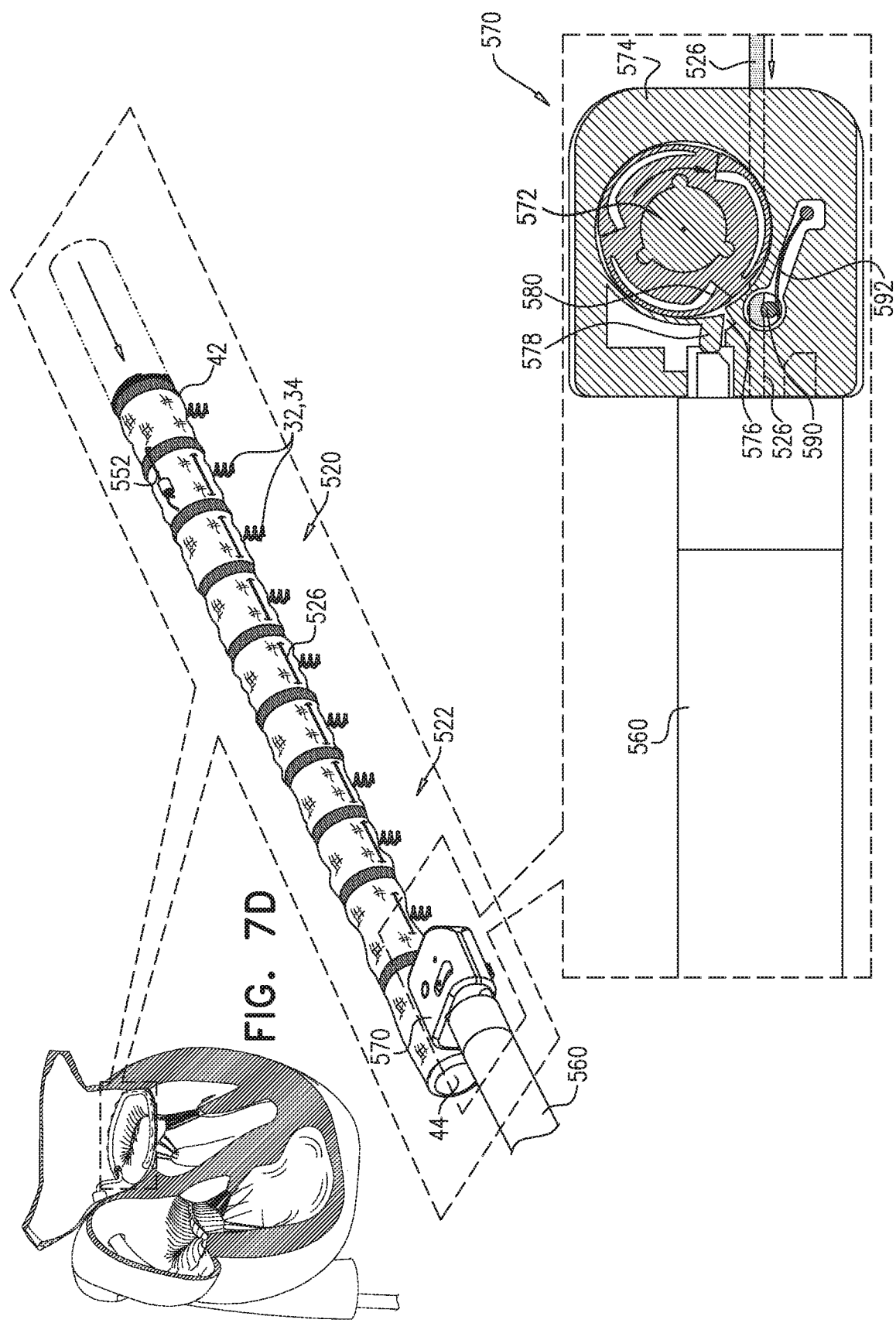

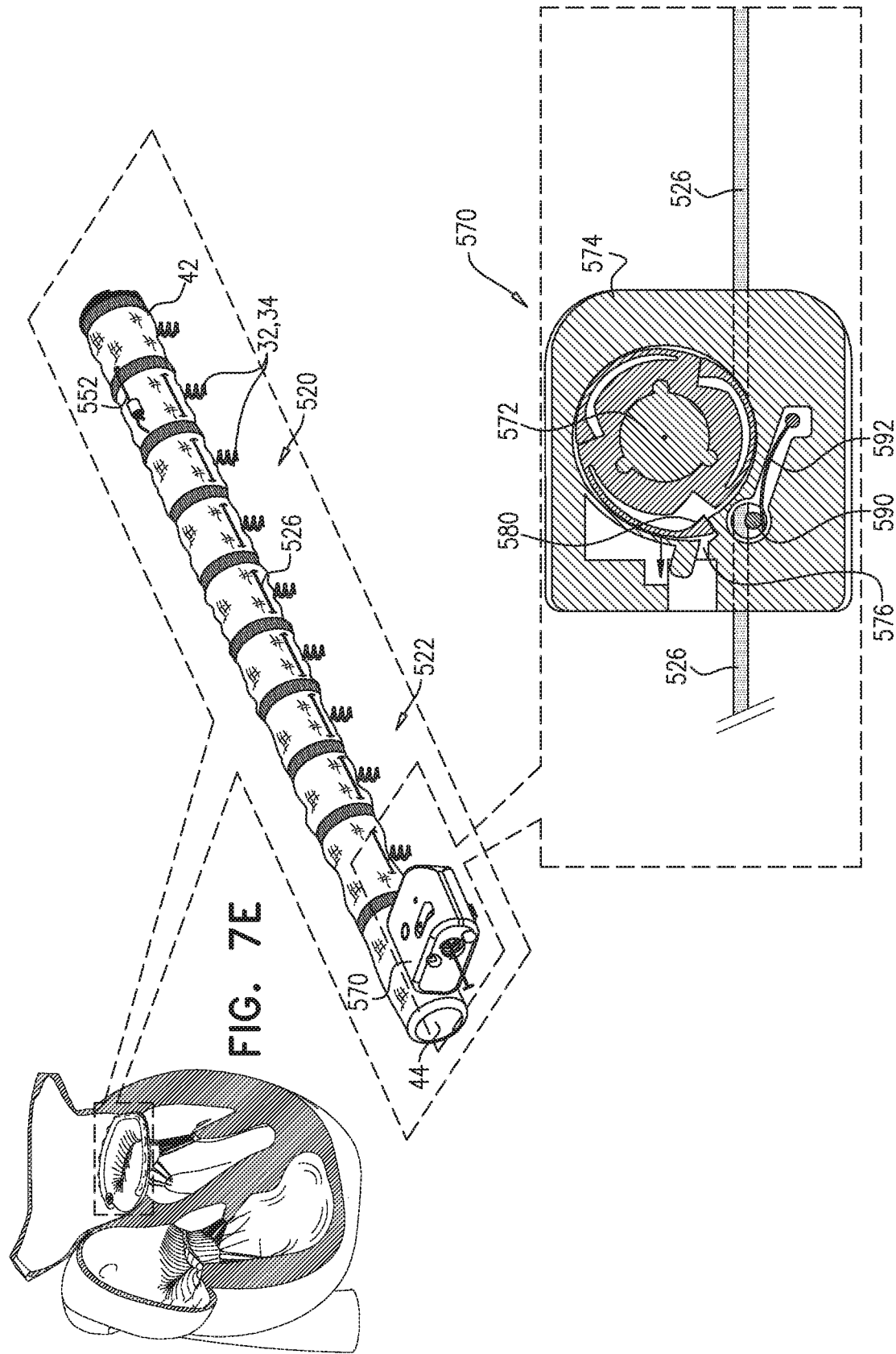

CONTRACTION OF AN ANNULOPLASTY STRUCTURE

CROSS-REFERENCES TO RELATED APPLICATIONS

The present application is a continuation of PCT patent application No. PCT/IL2019/050092 filed on Jan. 23, 2019, which claims priority from U.S. Provisional Patent Application 62/621,280 to Peleg et al., filed Jan. 24, 2018, each of which is incorporated herein by reference for all purposes.

FIELD OF THE INVENTION

Some applications of the present invention relate in general to adjustment of an implant. For example, some applications of the present invention relate to contraction of a cardiovascular implant, such as an annuloplasty structure.

BACKGROUND

Ischemic heart disease causes atrioventricular valve regurgitation by the combination of ischemic dysfunction of the papillary muscles, and the dilatation of the ventricle that is present in ischemic heart disease, with the subsequent displacement of the papillary muscles and the dilatation of the valve annulus.

Dilation of the annulus of an atrioventricular valve can prevent the valve leaflets from fully coapting when the valve is closed. Regurgitation of blood from the ventricle into the atrium can result in increased total stroke volume and decreased cardiac output, and ultimate weakening of the ventricle secondary to a volume overload and a pressure overload of the atrium.

Annuloplasty, such as by implantation of an annuloplasty ring, can be used to improve leaflet coaptation by adjusting the shape of the atrioventricular valve annulus. Percutaneous (e.g., transfemoral, transseptal, etc.) annuloplasty devices can be beneficial.

SUMMARY OF THE INVENTION

This summary is meant to provide some examples and is not intended to be limiting of the scope of the invention in any way. For example, any feature included in an example of this summary is not required by the claims, unless the claims explicitly recite the features. Also, the features described can be combined in a variety of ways. The description herein relates to systems, assemblies, methods, devices, apparatuses, combinations, etc. that can be used for reshaping the heart and/or a portion thereof. Various features and steps as described elsewhere in this disclosure can be included in the examples summarized here.

An adjustable annuloplasty band, comprising a sleeve and a contracting wire, is contracted by tensioning the contracting wire. In an exemplary application, the resulting excess of the contraction wire is deposited within the lumen of the sleeve, obviating the need to remove the excess from the implant, e.g., by cutting. Contraction of the annuloplasty band can therefore achieved by pulling the contraction wire into and/or increasing a longitudinal proportion of the contraction wire that is disposed within the lumen. The contraction can be maintained by locking a locking mechanism to the wire.

For some applications, the contraction wire is pulled into the lumen from within the lumen. For some applications, the contraction wire is pulled from outside the lumen. For some applications, the contraction wire is fed into the lumen using an adjustment mechanism.

There is therefore provided, in an exemplary application, a system or an apparatus for use at a heart of a subject, the system/apparatus including an annuloplasty band that includes:

A flexible sleeve having a first sleeve-end-portion, a second sleeve-end-portion, and a circumferential wall that defines a longitudinal lumen between the first and second sleeve-end-portions.

An elongate contraction wire having a first wire-end and a second wire-end, the first wire-end being attached to the sleeve at the first sleeve-end-portion, and the wire extending, in association with the circumferential wall, from the first sleeve-end-portion to the second sleeve-end-portion.

The wire can be arranged with respect to the sleeve such that pulling the contraction wire into and/or increasing a longitudinal proportion of the wire that is disposed within the lumen longitudinally contracts the sleeve.

In an application, the second wire-end is disposed within the lumen, and the wire is arranged with respect to the sleeve such that movement of the second wire-end toward the first sleeve-end-portion increases the longitudinal proportion of the wire that is disposed within the lumen by drawing the wire into the lumen.

In an application, the system/apparatus includes a contraction tool that includes a wire-engaging element. The wire-engaging element can be movable longitudinally into the lumen and through the lumen to the second wire-end, and can be reversibly couplable (e.g., within the lumen or outside the lumen), to the second wire-end. While coupled to the second wire-end, the wire-engaging element can be movable longitudinally toward the first sleeve-end-portion, such that the second wire-end is moved toward the first sleeve-end-portion, thereby drawing the wire into the lumen and longitudinally contracting the sleeve.

In an application, the wire extends from the first sleeve-end-portion to the second sleeve-end-portion in association with the circumferential wall, by weaving along the circumferential wall between the first sleeve-end-portion and the second sleeve-end-portion.

In an application, the system/apparatus includes a one-way mechanism, coupled to the wire, configured to allow one-way movement of the wire through the one-way mechanism, and coupled to the sleeve at the second sleeve-end-portion in an arrangement that (i) allows pulling the wire into and/or increasing the longitudinal proportion of the wire that is disposed within the lumen, and (ii) inhibits reducing the longitudinal proportion of the wire that is disposed within the lumen.

The system/apparatus can further include an attachment means, such as a plurality of anchors. In some applications, the system/apparatus includes a plurality of anchors with each anchor of the plurality of anchors being independently advanceable into the lumen, and configured to anchor the sleeve to tissue by being driven through the circumferential wall and into tissue. In some applications, the system/apparatus includes a plurality of anchors, and each anchor of the plurality of anchors can include an anchor head and a tissue-engaging element, can be independently advanceable into the lumen, and can be configured to anchor the sleeve to tissue by the tissue-engaging element being driven through the circumferential wall and into the tissue while the anchor head remains in the lumen.

The system/apparatus can include a contraction tool that includes a wire-engaging element, and the wire-engaging element, subsequently to anchoring of the sleeve using the anchors. The contraction tool can be movable longitudinally into the lumen and through the lumen to the second wire-end, and can be reversibly couplable (e.g., within the lumen or outside the lumen), to the second wire-end. While coupled to the second wire-end, it can be movable longitudinally through the lumen and past the anchor heads toward the first sleeve-end-portion, such that the second wire-end is moved toward the first sleeve-end-portion, thereby drawing the wire into the lumen and longitudinally contracting the sleeve.

In an application, the system/apparatus includes a locking mechanism, such as a lock, etc. The locking mechanism can include an unlocked state in which the locking mechanism allows movement of the wire through the locking mechanism, and pulling the wire into and/or increasing of the longitudinal proportion of the wire that is disposed within the lumen, and a locked state in which the locking mechanism inhibits movement of the wire through the locking mechanism.

In an application, the locking mechanism is a component of the annuloplasty band and is coupled to the sleeve, and the annuloplasty band is transluminally-advanceable to the heart with the locking mechanism coupled to the sleeve.

The locking mechanism can be disposed outside of the lumen or be disposed inside the lumen. In an application, the locking mechanism is coupled to the sleeve at the second sleeve-end-portion.

In an application, the apparatus includes a contraction tool that includes a wire-engaging element. The wire-engaging element can be movable longitudinally into the lumen and through the lumen to the second wire-end. The wire-engaging element can also be reversibly couplable (e.g., within the lumen or outside the lumen), to the second wire-end. While coupled to the second wire-end, the wire-engaging element can be movable longitudinally toward the first sleeve-end-portion, such that the second wire-end is moved toward the first sleeve-end-portion, thereby drawing the wire into the lumen and longitudinally contracting the sleeve.

The locking mechanism can be coupled to the contraction tool, and can be advanceable, using the contraction tool, longitudinally through the lumen toward the second sleeve-end-portion and the wire.

In an application, the apparatus includes a lock tool that engages the locking mechanism, and is configured to transition the locking mechanism into the locked state. The lock tool can be configured to engage the locking mechanism outside the lumen or within the lumen.

In an application, the locking mechanism is biased to assume the locked state. In an application, the lock tool is configured to retain the locking mechanism in the unlocked state while the lock tool is engaged with the locking mechanism, and the lock tool is configured to transition the locking mechanism into the locked state by disengaging from the locking mechanism.

In an application, the annuloplasty band further includes an adjustment mechanism, the adjustment mechanism coupled to the sleeve at the second sleeve-end-portion, and coupled to the wire. The adjustment mechanism can be configured such that actuation of the adjustment mechanism increases the longitudinal proportion of the wire that is disposed within the lumen by feeding the wire into the lumen.

In an application, the adjustment mechanism includes a capstan. In an application, the adjustment mechanism is configured not to collect the wire upon actuation of the adjustment mechanism.

In an application, the apparatus further includes a guide tube, extending from the adjustment mechanism into the lumen, the actuation of the adjustment mechanism feeding the wire into the lumen by feeding the wire into the tube.

In an application, the apparatus further includes a guide tube, disposed within the lumen, and the actuation of the adjustment mechanism feeds the wire into the tube.

There is further provided, in an exemplary application, a method, the method including securing an annuloplasty band on an annulus of a valve of a subject. The annuloplasty band including (i) a flexible sleeve that defines a longitudinal lumen therethrough, and (ii) an elongate contraction wire. The method also includes subsequently, longitudinally contracting the sleeve. In an application, this is done by pulling the contraction wire into and/or increasing a longitudinal proportion of the contraction wire that is disposed within the lumen, by drawing the contraction wire into the lumen.

In an application, the sleeve includes a circumferential wall that defines the lumen, and securing the annuloplasty band on the annulus includes sequentially, for each anchor of a plurality of anchors: advancing the anchor into the lumen, and driving a tissue-engaging element of the anchor through the circumferential wall and into the annulus, such that an anchor head of the anchor remains in the lumen.

In an application, the sleeve has a first sleeve-end and a second sleeve-end, and the contraction wire has a first wire-end and a second wire-end, and longitudinally contracting the sleeve includes bringing the second wire-end closer to the first sleeve-end.

In an application, the method further includes, subsequently to the step of longitudinally contracting the sleeve, maintaining a contraction state of the sleeve by locking a locking mechanism to the contraction wire. The locking mechanism can be a component of the annuloplasty band, and can be coupled to the sleeve, and have an unlocked state and a locked state.

Securing the annuloplasty band on the annulus can include securing, to the annulus, the annuloplasty band having the locking mechanism coupled to the sleeve.

In an application, the step of longitudinally contracting the sleeve includes longitudinally contracting the sleeve by pulling the contraction wire into and/or increasing the longitudinal proportion of the contraction wire that is disposed within the lumen, by drawing the contraction wire into the lumen while the locking mechanism is in the unlocked state.

The method can further include, subsequently to longitudinally contracting the sleeve, transitioning the locking mechanism into its locked state.

In an application, the locking mechanism is coupled to the sleeve and is disposed outside of the lumen, and securing the annuloplasty band on the annulus includes securing, to the annulus, the annuloplasty band having the locking mechanism coupled to the sleeve and disposed outside of the lumen.

In an application, the method further includes advancing a wire-engaging element of a contraction tool longitudinally into and through the lumen, and coupling (e.g., within the lumen or outside the lumen), the wire-engaging element to the wire, and the step of longitudinally contracting the sleeve includes longitudinally contracting the sleeve by increasing the longitudinal proportion of the contraction wire that is disposed within the lumen, by pulling the contraction wire into the lumen using the contraction tool.

In an application, advancing the wire-engaging element of the contraction tool includes advancing the locking mechanism into the lumen while the locking mechanism is coupled to the contraction tool, and locking the locking mechanism to the contraction wire includes locking the locking mechanism to the contraction wire within the lumen.

In an application, the contraction tool includes a lock tool that maintains the locking mechanism in an unlocked state, and locking the locking mechanism to the contraction wire includes allowing the lock to transition into a locked state by disengaging the lock tool from the locking mechanism.

In an application, the sleeve includes a circumferential wall that defines the lumen, and securing the annuloplasty band on the annulus includes sequentially, for each anchor of a plurality of anchors:

advancing the anchor into the lumen, and
driving a tissue-engaging element of the anchor through the circumferential wall and into the annulus, such that an anchor head of the anchor remains in the lumen, and
advancing the wire-engaging element of the contraction tool longitudinally into and through the lumen includes advancing the wire-engaging element of the contraction tool longitudinally into and through the lumen and past the anchor heads within the lumen.

In an application, locking the locking mechanism to the contraction wire includes transitioning the locking mechanism into a locked state using a lock tool that is engaged with the locking mechanism outside of the lumen.

In an application, locking the locking mechanism to the contraction wire includes disengaging a lock tool from the locking mechanism, the locking mechanism being biased to assume a locked state, and the lock tool being configured to retain the locking mechanism in an unlocked state while the lock tool is engaged with the locking mechanism.

In an application, drawing the contraction wire into the lumen includes moving an end of the contraction wire longitudinally through the lumen.

In an application, moving the end of the contraction wire longitudinally through the lumen includes pulling the end of the contraction wire longitudinally through the lumen.

In an application, pulling the end of the contraction wire longitudinally through the lumen includes using a tool, coupled to the end of the contraction wire, to pull the end of the contraction wire longitudinally through the lumen.

In an application, moving the end of the contraction wire longitudinally through the lumen includes pushing the end of the contraction wire longitudinally through the lumen.

In an application, the annuloplasty band further includes an adjustment mechanism coupled to the sleeve and to the wire, and the step of longitudinally contracting the sleeve includes feeding the contraction wire into the lumen by actuating the adjustment mechanism.

In an application, actuating the adjustment mechanism includes actuating the adjustment mechanism using an adjustment tool, and the method further includes disengaging the adjustment tool from the adjustment mechanism subsequently to actuating the adjustment mechanism.

In an application, the method further includes, subsequently to securing the annuloplasty band on the annulus, and prior to actuating the adjustment mechanism, advancing the adjustment tool to the annuloplasty band and engaging the adjustment mechanism with the adjustment tool.

In an application, the adjustment mechanism includes a rotatable element, and actuating the adjustment mechanism includes rotating the rotatable element.

In an application, the rotatable element is a capstan, and rotating the rotatable element includes rotating the capstan.

In an application, actuating the adjustment mechanism includes actuating the adjustment mechanism without collecting the wire on the adjustment mechanism.

In an application, the annuloplasty band further includes a guide tube, extending from the adjustment mechanism into the lumen, and feeding the contraction wire into the lumen by actuating the adjustment mechanism includes feeding the contraction wire into the tube by actuating the adjustment mechanism.

There is further provided, a system or an apparatus for use at a heart of a subject, the system/apparatus comprising an annuloplasty structure that comprises a flexible sleeve having a first sleeve-end-portion, a second sleeve-end-portion, and a circumferential wall that defines a longitudinal lumen between the first and second sleeve-end-portions. The annuloplasty structure also includes an elongate contraction wire having a first wire-end and a second wire-end, the first wire-end being attached to the sleeve at the first sleeve-end-portion, and the wire extending, in association with the circumferential wall, between the first sleeve-end-portion to the second sleeve-end-portion.

The system/apparatus can also include an adjustment mechanism, which can be coupled to the sleeve. In some applications, the adjustment mechanism a pulley system comprising at least a first pulley and a second pulley. Though, in some applications, the pulley system can comprises at least three pulleys, at least four pulleys, at least five pulleys, at least six pulleys, or more.

In some applications, the system/apparatus can also include an actuator, mechanically coupled to the pulley system such that actuation of the actuator adjusts a distance between the first pulley and the second pulley. The actuator can be a linear actuator. The actuator can comprise a rotational element, and is actuated via rotation of the rotational element.

The wire is arranged with respect to the sleeve and the adjustment mechanism such that drawing the wire into the adjustment mechanism longitudinally contracts the sleeve.

In some applications, the pulley system is engaged with the wire such that increasing the distance between the first and second pulleys draws the wire into the adjustment mechanism, thereby longitudinally contracting the sleeve.

The pulley system and the wire can be configured to mechanically cooperate such that increasing the distance by a distance-increase amount draws, into the adjustment mechanism, a portion of the wire that is longer than the distance-increase amount, such as a portion of the wire that is at least twice as long as the distance-increase amount or more (e.g., at least four times as long, at least six times as long, etc.).

The pulley system and the wire can be configured to mechanically cooperate such that increasing the distance by a distance-increase amount longitudinally contracts the sleeve by a contraction length that is greater than the distance-increase amount, such as by a contraction length that is at least twice as great as the distance-increase amount or more (e.g., at least four times as great, at least six times as great, etc.).

There is further provided, a system or an apparatus for use at a heart of a subject, the system/apparatus including an implant having a first portion and a second portion. The implant comprises a contraction wire having a first wire-end and a second wire-end, the first wire-end being attached to the first portion, and the wire extending from the first portion to the second portion. The implant further comprises an adjustment mechanism, which can be coupled to the contraction wire.

In some applications, the adjustment mechanism includes a pulley system including at least a first pulley and a second pulley.

In some applications, the adjustment mechanism includes an actuator, mechanically coupled to the pulley system such that actuation of the actuator adjusts a distance between the first pulley and the second pulley.

The wire can be arranged with respect to the first portion, the second portion, and the adjustment mechanism, such that drawing the wire into the adjustment mechanism draws the first portion and the second portion closer together. In an application, the wire is arranged in a back-and-forth arrangement within the adjustment mechanism.

The pulley system can be engaged with the wire such that increasing the distance between the first and second pulleys draws the wire into the adjustment mechanism, thereby drawing the first portion and the second portion closer together.

In an application, the implant includes a flexible sleeve having a circumferential wall that defines a longitudinal lumen between the first and second portions.

In an application, the adjustment mechanism further includes a housing that houses the pulley system and the actuator.

The pulley system can include any number of pulleys. In an application, the pulley system includes at least three pulleys. The pulley system can include at least four pulleys or at least five pulleys as well.

In an application, the pulley system and the wire mechanically cooperate such that increasing the distance by a distance-increase amount draws, into the adjustment mechanism, a portion of the wire that is longer than the distance-increase amount.

In an application, the pulley system and the wire mechanically cooperate such that increasing the distance by the distance-increase amount draws, into the adjustment mechanism, a portion of the wire that is at least twice as long as the distance-increase amount. In an application, the pulley system and the wire mechanically cooperate such that increasing the distance by the distance-increase amount draws, into the adjustment mechanism, a portion of the wire that is at least four times as long as the distance-increase amount. In an application, the pulley system and the wire mechanically cooperate such that increasing the distance by the distance-increase amount draws, into the adjustment mechanism, a portion of the wire that is at least six times as long as the distance-increase amount.

In an application, the pulley system and the wire mechanically cooperate such that increasing the distance by a distance-increase amount draws the first portion and the second portion closer together by a contraction length that is greater than the distance-increase amount.

In an application, the pulley system and the wire mechanically cooperate such that increasing the distance by the distance-increase amount draws the first portion and the second portion closer together by a contraction length that is at least twice as great as the distance-increase amount. In an application, the pulley system and the wire mechanically cooperate such that increasing the distance by the distance-increase amount draws the first portion and the second portion closer together by a contraction length that is at least four times greater than the distance-increase amount. In an application, the pulley system and the wire mechanically cooperate such that increasing the distance by the distance-increase amount draws the first portion and the second portion closer together by a contraction length that is at least six times greater than the distance-increase amount.

In an application, the first pulley includes a first wheel and the second pulley includes a second wheel. In an application, the first wheel and the second wheel are unpowered, and are configured to rotate passively in response to the wire moving thereover.

In an application, the actuator is a linear actuator, and can be a leadscrew, etc.

In an application, the actuator includes a rotational element, and is actuated via rotation of the rotational element.

In an application, the system/apparatus further includes a tool that is (i) transluminally advanceable to the implant, (ii) intracorporeally reversibly engageable with the rotational element, and (iii) while engaged with the rotational element, configured to rotate the rotational element.

There is further provided, a system or an apparatus for use at a heart of a subject, the system/apparatus including an implant. The implant including a flexible sleeve having a first sleeve-end-portion, a second sleeve-end-portion, and a circumferential wall that defines a longitudinal lumen between the first and second sleeve-end-portions. The implant can also include a lock, coupled to the sleeve, the lock including a passive capstan. The implant includes an elongate contraction wire or other contraction element.

The contraction wire/element can be attached to the first sleeve-end portion, and can extend (i) from the first sleeve-end-portion to the second sleeve-end-portion in association with the circumferential wall, and (ii) through the lock, wrapping at least once around the capstan, and (iii) away from the lock and the sleeve.

The association between the wire and the sleeve can be such that pulling progressive regions of the wire away from the sleeve via the lock progressively longitudinally contracts the sleeve.

The wrapping of the contraction wire around the capstan can be such that movement of the wire through the lock rotates the capstan.

The lock can:
have a discrete unlocked state in which the capstan is rotatable, thereby facilitating movement of the wire through the lock,
have a discrete locked state in which rotation of the capstan is locked in at least one direction, thereby preventing movement of the wire through the lock, and
be reversibly switchable between the unlocked state and the locked state.

In an application, the lock is biased toward being in the locked state.

In an application, the lock further includes a mechanical resistor that is configured to partially resist movement of the wire through the lock, independent of whether the lock is in the unlocked state or the locked state.

In an application, in the locked state, rotation of the capstan is bidirectionally locked. In an application, in the locked state, rotation of the capstan is unidirectionally locked.

In an application, the implant is transluminally implantable in the heart of the subject.

In an application, the system/apparatus further includes an adjustment tool that is transluminally advanceable to the transluminally-implanted implant.

In an application, the adjustment tool is engageable with the lock, and is configured to switch the lock between the unlocked state and the locked state.

In an application, the tool is further configured to contract the sleeve by pulling on the wire.

In an application, the system/apparatus further includes a guide member that includes a flexible tube, a distal portion of the guide member reversibly coupled to the lock, the wire extends away from the lock and the sleeve via the tube, and the tool is transluminally advanceable to the transluminally-implanted implant by being advanced distally over the tube to the lock.

In an application, the lock further includes a housing that houses the capstan, the capstan is rotationally coupled to the housing, and movement of the wire through the lock rotates the capstan with respect to the housing.

In an application, in the unlocked state, the capstan is bidirectionally rotatable with respect to the housing.

In an application, the lock further includes at least one detent that is biased to rotationally lock the capstan with respect to the housing.

In an application, the at least one detent is attached to the capstan, and is configured to rotationally lock the capstan with respect to the housing, by engaging the housing.

In an application: the housing is shaped to define a recess, the at least one detent is configured to engage the housing by protruding into the recess, and the housing includes a button that, when pressed, switches the lock into the unlocked state by obstructing the detent from engaging the recess.

In an application, the at least one detent is biased to rotationally lock the capstan in a plurality of rotational positions with respect to the housing.

In an application, the at least one detent is a plurality of detents, each detent of the plurality of detents being biased to rotationally lock the capstan in a corresponding rotational position with respect to the housing.

Other features and components and steps described elsewhere herein can also be used with and/or added to the systems, apparatuses, and methods described above.

The present invention will be more fully understood from the following detailed description of applications thereof, taken together with the drawings, in which:

BRIEF DESCRIPTION OF THE DRAWINGS

FIGS. 1A-E are schematic illustrations of an exemplary annuloplasty system for treating a native heart valve;

FIGS. 2A-E are schematic illustrations of an exemplary annuloplasty system for treating the native heart valve;

FIGS. 3A-D are schematic illustrations of an exemplary annuloplasty system for treating the native heart valve;

FIGS. 4A-D are schematic illustrations of an exemplary annuloplasty system for treating the native heart valve;

FIGS. 5A-C are schematic illustrations of an exemplary annuloplasty system for treating the native heart valve; and FIGS. 6A-D and 7A-E are schematic illustrations of an exemplary annuloplasty system for treating the native heart valve.

DETAILED DESCRIPTION OF EMBODIMENTS

Figure 6A:
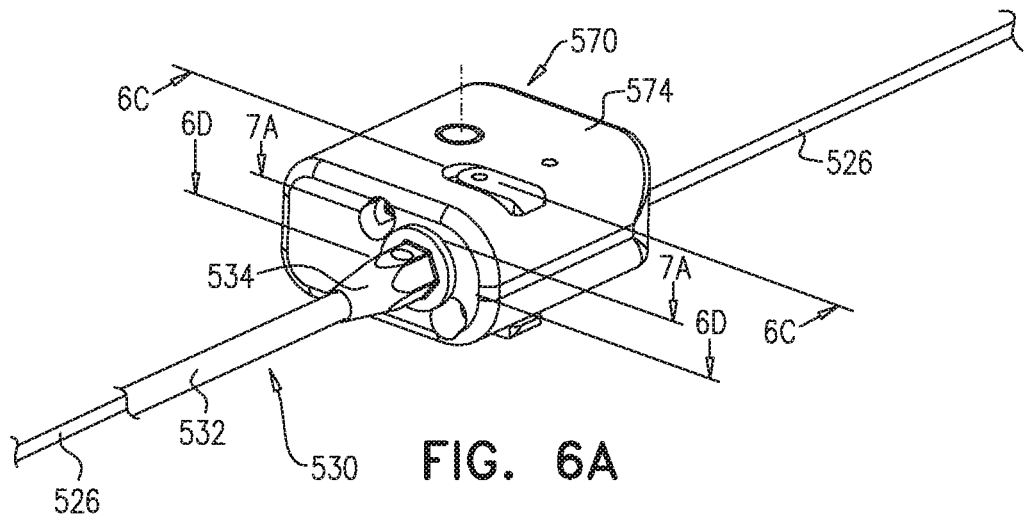
Figure 6B:
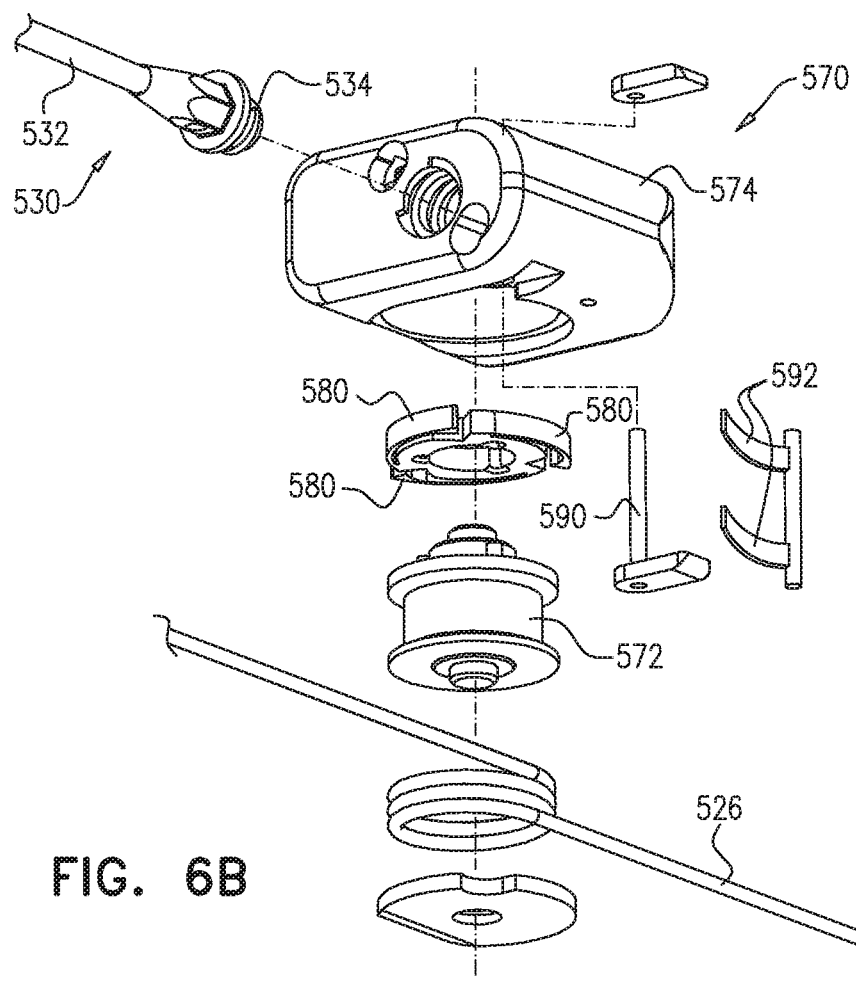
Figure 6C:
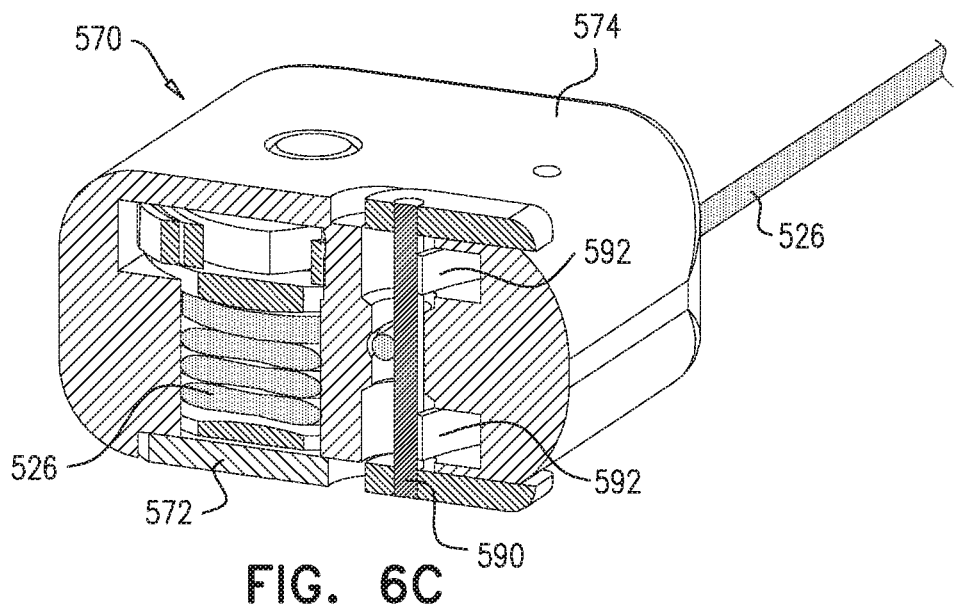
Figure 6D:
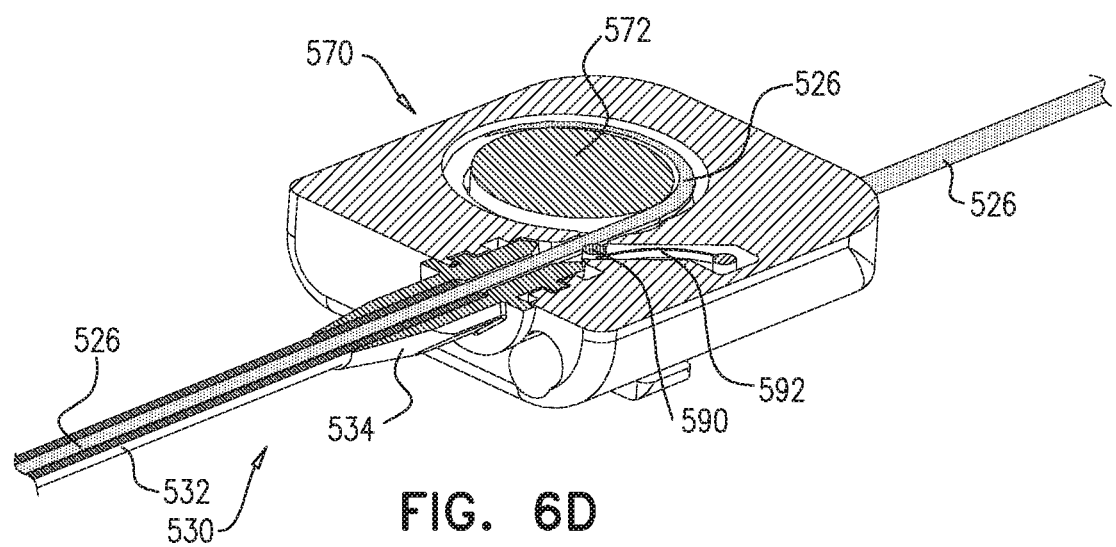

Reference is made to FIGS. 1A-E, which are schematic illustrations of an exemplary annuloplasty system 20 that comprises an implant 22. System 20 is for treating a native valve 10 (e.g., an atrioventricular valve, such as the mitral valve or the tricuspid valve) of a heart 4 of a subject. Any and all of the methods, techniques, steps, etc. described herein using system 20 can be performed on a living animal or on a non-living cadaver, cadaver heart, simulator, anthropomorphic ghost, etc.

Implant 22 comprises an implant body 24, which can be an annuloplasty structure, such as an annuloplasty band or an annuloplasty ring. Implant body 24 comprises a flexible sleeve 25. Sleeve 25 has a first sleeve-end-portion 42, a second sleeve-end-portion 44, and a circumferential wall 46. Circumferential wall 46 can define a longitudinal lumen 48, for example between the first and second sleeve-end-portions. Circumferential wall 46 can be made of a fabric, such as a polyethylene terephthalate fabric, e.g., Dacron™. Implant 22 further comprises an elongate contraction wire or member 26. It is to be noted that the term "wire" is not intended to limit wire 26 to being metallic, nor to limit the number of strands that it may comprise. For some applications, contraction wire comprises one or more strands of metal. For some applications, contraction wire 26 comprises one or more strands of polymer. For some applications, contraction wire 26 is braided or woven. For some applications, contraction wire 26 is coated with a low-friction coating, such as polytetrafluoroethylene (PTFE).

Implant body 24 can be configured to be placed partially or completely around an annulus of valve 10. Implant body 24 can be attached to tissue (e.g., tissue of a heart valve annulus, etc.) in a variety of ways, such as with anchors, sutures, clips, and/or other attachment means. In some embodiments, the implant body 24 is configured to be anchored in place using a plurality of (e.g., 5-20) tissue anchors 32. In one embodiment, each tissue anchor comprises a tissue-coupling element 34, and a tool-engaging head 36 fastened to an end of the tissue-coupling element. In some embodiments, following introduction of implant body 24 into the subject, each anchor 32 is sequentially (and typically independently) intracorporeally delivered into the lumen of the sleeve, and its tissue-coupling element 34 is driven through the circumferential wall and into tissue of the valve annulus, thereby anchoring the sleeve to the valve annulus. Subsequent to attachment to the tissue, longitudinal contraction of implant body 24 circumferentially tightens the valve annulus, thereby improving coaptation of the valve leaflets, and reducing regurgitation.

For some applications, the annuloplasty structure of implant body 24 is, or shares features with, mutatis mutandis, the annuloplasty structure(s) described in one or more of the following publications, which are incorporated herein by reference. For some applications, implant 22 is implanted as described in one or more of these publications, mutatis mutandis:

PCT application publication WO 2010/128503 to Zipory et al.

PCT application publication WO 2012/176195 to Gross et al.

PCT application publication WO 2013/069019 to Sheps et al.

PCT application publication WO 2014/064694 to Sheps et al.

Contraction wire 26 has a first wire-end 52 and a second wire-end 54. In some embodiments, first wire-end 52 is attached (e.g., fixedly attached) to sleeve 25 at first sleeve-end-portion 42, and wire 26 extends, in association with the circumferential wall of the sleeve, from the first sleeve-end-portion to second sleeve-end-portion 44. In some embodiments, and as shown, the association between wire 26 and circumferential wall 46 is provided by the wire being woven along or as part of the circumferential wall between first sleeve-end-portion 42 and second sleeve-end-portion 44.

As shown, sleeve-end-portions 42 and 44 can include more than just the very ends of sleeve 25. Similarly, wire 26 may not extend all the way to the ends of sleeve 25. As shown, at least one anchor 32 can be placed within at least one of sleeve-end-portions 42 and 44, beyond wire 26.

As described in more detail hereinbelow, wire 26 is arranged with respect to sleeve 25 such that pulling a longitudinal proportion of the wire into the lumen and/or increasing the amount that is disposed within the lumen longitudinally contracts the sleeve. Optionally, an end 54 of the wire 26 can be positioned inside the lumen.

FIG. 1A schematically shows implant 22 following its implantation at valve 10, with the tissue-coupling element 34 of each anchor 32 extending through the circumferential wall of sleeve 25 and into the annulus of the valve. For the sake of clarity, the tissue into which tissue-coupling elements 34 penetrates is not shown. As shown, second wire-end 54 can be disposed within the lumen of sleeve 25 prior to and/or during implantation, or can be disposed outside the lumen but be pullable into the lumen. For some applications, and as shown, system 20 further comprises an elongate guide member 28, reversibly coupled to second wire-end 54, and extending proximally though the lumen of sleeve 25, and proximally away from implant 22 (e.g., out of the subject).

Following implantation of implant 22, a contraction tool 60 is used to facilitate contraction of the implant. Contraction tool 60 comprises a wire-engaging element 62, which is movable longitudinally into lumen 48, and through the lumen to second wire-end 54. Such movement is shown in FIG. 1B. For applications in which implant body 24 is anchored using anchors 32, tool 60 is dimensioned to be advanceable through lumen 48 past anchor heads 36 already disposed within the lumen.

Wire-engaging element 62 is reversibly couplable, e.g., within lumen 48, to second wire-end 54. Such coupling is shown in FIG. 1C. Implant 22 can comprise an appendage 55 coupled to second wire-end 54 of contraction wire 26, wire-engaging element 62 and appendage 55 being mutually configured to facilitate the reversible coupling of the wire-engaging element to the second wire-end of the contraction wire. While coupled to second wire-end 54, wire-engaging element 62 is movable longitudinally toward first sleeve-end-portion 42 (e.g., by being pulled proximally), such that the second wire-end is moved toward the first sleeve-end-portion, thereby drawing contraction wire 26 into lumen 48, and longitudinally contracting sleeve 25 (FIG. 1D).

System 20 further comprises a locking mechanism 70, coupled to contraction tool 60, and advanceable, using the contraction tool, longitudinally through lumen 48 toward second sleeve-end-portion 44 and contraction wire 26 (e.g., as shown in FIGS. 1B-C). In some embodiments, locking mechanism 70 has (i) an unlocked state in which the locking mechanism allows movement of contraction wire 26 through the locking mechanism, and increasing of the longitudinal proportion of the wire that is disposed within the lumen, and (ii) a locked state in which the locking mechanism inhibits movement of the wire through the locking mechanism.

Once a desired amount of contraction of sleeve 25 has been achieved by drawing contraction wire 26 into lumen 48 (and through locking mechanism 70), locking mechanism 70 is locked, e.g., using tool 60, which thereby also serves as a lock tool 64 that engages locking mechanism 70 within lumen 48. The locking of locking mechanism 70 inhibits the contraction wire from moving back out of the lumen, and therefore maintaining the desired amount of contraction of the sleeve. For example, locking mechanism 70, locked to contraction wire 26, may be too large to exit lumen 48 via the hole through which wire 26 entered the lumen at second sleeve-end-portion 44.

Tool 60 may then be decoupled from wire 26, and removed from implant 22 (FIG. 1E). For applications in which system 20 comprises guide member 28, the guide member is also decoupled from implant 22, e.g., facilitated by tool 60.

It is to be noted that the resulting excess 56 of wire 26 (i.e., the part of the wire that has passed through locking mechanism 70 and does not serve to maintain the contraction of sleeve 25, e.g., the part of the wire that is not under tension) is disposed within lumen 48. The inventors hypothesize that this, in contrast to a hypothetical similar implant in which the excess of the contraction wire is disposed outside of sleeve 25, advantageously does not require removal of the excess of the contraction wire (e.g., by cutting).

Reference is now made to FIGS. 2A-E, which are schematic illustrations of an annuloplasty system 120 for treating native valve 10, in accordance with some applications of the invention. System 120 comprises an implant 122, which comprises implant body 24 (comprising sleeve 25) and contraction wire 26, e.g., as described hereinabove, mutatis mutandis. Typically, except where noted, implant 122 and the implantation thereof are as described hereinabove for implant 22 and its implantation, mutatis mutandis.

As described for implant 22, wire 26 of implant 122 can be arranged with respect to sleeve 25 such that pulling wire 26 into the lumen and/or increasing a longitudinal proportion of the wire that is disposed within the lumen longitudinally contracts the sleeve.

FIGS. 2A-E show system 120 not comprising a guide member such as guide member 28, described hereinabove. However, in some embodiments, system 120 may in fact comprise a guide member, and/or system 20 may not comprise a guide member.

System 120 comprises a locking mechanism 170. However, in contrast to locking mechanism 70 of system 20, locking mechanism 170 of system 120 is a component of implant 122, and implant 122 is transluminally-advanceable to the heart with the locking mechanism coupled to sleeve 25, typically at second sleeve-end-portion 44. In some embodiments, at least part of (e.g., all of) locking mechanism 170 is disposed outside of lumen 48.

System 120 comprises a lock tool 164 that engages locking mechanism 170, and is configured to transition the locking mechanism into the locked state. However, in contrast to lock tool 164 of system 20, lock tool 164 of system 120 engages locking mechanism 170 outside lumen 48. For some applications, locking mechanism 170 is biased to assume its locked state, and lock tool 164 is configured to retain the locking mechanism in its unlocked state while the lock tool is engaged with the locking mechanism. For such applications, disengagement of lock tool 164 from locking mechanism 170 allows the locking mechanism to transition into its locked state. Other locking mechanisms and lock tools described herein may also operate in this manner, mutatis mutandis.

FIG. 2A schematically shows implant 122 following its implantation at valve 10, with the tissue-coupling element 34 of each anchor 32 extending through the circumferential wall of sleeve 25 and into the annulus of the valve. For the sake of clarity, the tissue into which tissue-coupling elements 34 penetrates is not shown. In some embodiments, as shown, second wire-end 54 is disposed within the lumen of sleeve 25 prior to and/or during implantation.

Following implantation of implant 122, a contraction tool 160 is used to facilitate contraction of the implant. Contraction tool 160 comprises a wire-engaging element 162, which is movable longitudinally into lumen 48, and through the lumen to second wire-end 54, to which it is then reversibly coupled (FIG. 2B). For applications in which implant body 24 is anchored using anchors 32, tool 160 is dimensioned to be advanceable through lumen 48 past anchor heads 36 already disposed within the lumen.

While coupled to second wire-end 54, wire-engaging element 162 is movable longitudinally toward first sleeve-end-portion 42 (e.g., by being pulled proximally), such that the second wire-end is moved toward the first sleeve-end-portion, thereby drawing contraction wire 26 into lumen 48, and longitudinally contracting sleeve 25 (FIG. 2C).

During the contraction of sleeve 25, locking mechanism 170 is in its unlocked state, e.g., maintained in the unlocked state by lock tool 164. Once a desired amount of contraction of sleeve 25 has been achieved by drawing contraction wire 26 into lumen 48 (and through locking mechanism 170), locking mechanism 170 is locked, e.g., using lock tool 164, typically by disengaging the lock tool from the locking mechanism (FIG. 2D). Tool 160 (e.g., wire-engaging element 162 thereof) can then be decoupled from wire 26, and removed from implant 22 (FIG. 2E). The resulting excess 56 of wire 26 is advantageously disposed within lumen 48, e.g., as described hereinabove for system 20, mutatis mutandis.

Reference is now made to FIGS. 3A-D, which are schematic illustrations of an annuloplasty system 220 for treating native valve 10, in accordance with some applications of the invention. System 220 comprises an implant 222, which comprises implant body 24 (comprising sleeve 25) and contraction wire 26, e.g., as described hereinabove, mutatis mutandis. Typically, except where noted, implant 222 and the implantation thereof are as described hereinabove for implant 22 and/or implant 122, mutatis mutandis.

As described for implants 22 and 122, wire 26 of implant 222 is arranged with respect to sleeve 25 such that pulling the wire 26 into the lumen and/or increasing a longitudinal proportion of the wire that is disposed within the lumen longitudinally contracts the sleeve.

Implant 222 comprises an adjustment mechanism 280 coupled to implant body 24 (e.g., to sleeve 25), for example at second sleeve-end-portion 44. Adjustment mechanism 280 is coupled to contraction wire 26, and is configured such that actuation of the adjustment mechanism increases the longitudinal proportion of the wire that is disposed within lumen 48 by feeding the wire into the lumen. For some applications, adjustment mechanism 280 is disposed outside of lumen 48. For some applications, adjustment mechanism 280 is disposed within lumen 48 or partially within the lumen. Typically, adjustment mechanism 280 is configured not to collect contraction wire 26 upon actuation of the adjustment mechanism. That is, actuation of adjustment mechanism 280 typically does not cause contraction wire 26 to collect on or in the adjustment mechanism. Rather, adjustment mechanism 280 moves contraction wire 26 from one side of the adjustment mechanism to the other side of the adjustment mechanism. For some applications, adjustment mechanism 280 is actuated by rotation. For example, and as shown in FIG. 3A, adjustment mechanism 280 can comprise a capstan 282, e.g., disposed within a housing 284. Whereas rotation of a spool would cause contraction wire 26 to collect upon the spool, rotation of capstan 282 does not collect the contraction wire, but instead a constant number of turns of the contraction wire around the capstan is maintained as the contraction wire is fed from one side of the capstan to the other.

It is hypothesized by the inventors that another particular advantage of using a capstan is that because the number of turns of the wire around the capstan is maintained, the amount of contraction induced per revolution of the capstan remains constant.

For some applications, implant 222 further comprises a guide tube 286, at least part of which is disposed within lumen 48. For example, guide tube 286 may extend from adjustment mechanism 280 into lumen 48. Guide tube 286 is narrower than sleeve 25. Actuation of adjustment mechanism 280 feeds contraction wire 26 into guide tube 286. For some applications, guide tube 286 is lined with a low-friction lining such as PTFE, to facilitate sliding of wire 26 through the tube. It is hypothesized by the inventors that tube 286 advantageously facilitates sliding of second wire-end 54 through lumen 48 toward first sleeve-end-portion 42.

FIG. 3A schematically shows implant 222 following its implantation at valve 10, with the tissue-coupling element 34 of each anchor 32 extending through the circumferential wall of sleeve 25 and into the annulus of the valve. For the sake of clarity, the tissue into which tissue-coupling elements 34 penetrates is not shown. In some embodiments, as shown, second wire-end 54 is disposed within the lumen of sleeve 25 prior to and/or during implantation.

Following implantation of implant 222, a contraction tool 260 is used to facilitate contraction of the implant by actuating adjustment mechanism 280. For applications in which adjustment mechanism 280 is actuated by rotation, contraction tool 260 comprises a rotation tool.

For some applications, implant 222 is implanted with contraction tool 260 coupled thereto (e.g., engaging adjustment mechanism 280).

For some applications, and as shown, system 220 can comprise an elongate guide member 228, reversibly coupled to implant 222 (e.g., to adjustment mechanism 280), and extending proximally away from implant 222 (e.g., out of the subject). Subsequent to implantation of implant 222, contraction tool 260 is advanced along (e.g., over) guide member 228 to adjustment mechanism 280 (FIG. 3B). While engaged with adjustment mechanism 280, contraction tool 260 actuates the adjustment mechanism, feeding contraction wire 26 into lumen 48 (e.g., into tube 286), typically moving second wire-end 54 toward first sleeve-end-portion 42 (FIG. 3C).

Subsequently, contraction tool 260 is disengaged from adjustment mechanism 280, and is removed from the subject (FIG. 3D). As shown, guide member 228, if used, is also decoupled from implant 222 (e.g., from adjustment mechanism 280) and removed from the subject. For some applications, contraction tool 260 is used to decouple guide member 228 from the implant.

For some applications, system 220 comprises a locking mechanism 270. In contrast to locking mechanism 70, and similar to locking mechanism 170, locking mechanism 270 of system 220 is a component of implant 222, and implant 222 is transluminally-advanceable to the heart with the locking mechanism coupled to sleeve 25, typically at second sleeve-end-portion 44. In some embodiments, locking mechanism 270 is coupled to adjustment mechanism 280, and can also be disposed within housing 284. In its unlocked state, locking mechanism 270 typically allows movement of contraction wire 26 into lumen 48 by allowing actuation of adjustment mechanism 270. In its locked state, locking mechanism 270 can inhibit movement of contraction wire 26 into lumen 48 by inhibiting actuation of adjustment mechanism 270.

For some applications, contraction tool 260 comprises or serves as a lock tool 264, and is configured to transition locking mechanism 270 into the locked state. For some applications, locking mechanism 270 is biased to assume its locked state, and lock tool 264 is configured to retain the locking mechanism in its unlocked state while the lock tool is engaged with the locking mechanism and/or adjustment mechanism 280.

Reference is now made to FIGS. 4A-D, which are schematic illustrations of an annuloplasty system 320 for treating native valve 10, in accordance with some applications of the invention. Except where noted, system 320 and its components are typically the same as system 20 and correspondingly-named components, mutatis mutandis. System 320 comprises an implant 322, which comprises implant body 24 (comprising sleeve 25) and a contraction wire 326, e.g., as described hereinabove, mutatis mutandis. Contraction wire 326 is similar to contraction wire 26, except that it extends proximally away from sleeve 25.

FIG. 4A schematically shows implant 322 following its implantation at valve 10, with the tissue-coupling element 34 of each anchor 32 extending through the circumferential wall of sleeve 25 and into the annulus of the valve. For the sake of clarity, the tissue into which tissue-coupling elements 34 penetrates is not shown. For some embodiments, as shown, contraction wire 326 extends through lumen 48 toward and past first sleeve-end-portion 42, and proximally away from the sleeve 25, such that second wire-end 54 is typically disposed outside of the subject.

Following implantation of implant 322, a contraction tool 360 is used to facilitate contraction of the implant. Contraction tool 360 is slid distally over contraction wire 326 toward implant 322 (FIG. 4B). Contraction wire 326 is pulled proximally, thereby contracting sleeve 25 (FIG. 4C). Contraction tool 360 can provide an opposing force against the proximal end of sleeve 25.

System 320 further comprises a locking mechanism 370 (e.g., a lock, etc.), coupled to contraction tool 360, and advanceable, using the contraction tool, longitudinally along contraction wire 326 to implant 322. Locking mechanism 370 has (i) an unlocked state in which the locking mechanism allows movement of contraction wire 326 through the locking mechanism, and (ii) a locked state in which the locking mechanism inhibits movement of the wire through the locking mechanism. Once a desired amount of contraction of sleeve 25 has been achieved, locking mechanism 370 is locked, e.g., using tool 360, which thereby also serves as a lock tool 364. The locking of locking mechanism 370 inhibits the contraction wire from returning, and therefore maintains the desired amount of contraction of sleeve 25. For example, locking mechanism 370, locked to contraction wire 326, may be too large to enter lumen 48. Tool 360 can then cut excess 356 of wire 326, and be removed from implant 22 (FIG. 1E).

It is to be noted that, unlike in systems 20, 120, and 220, in system 320 the excess 356 of contraction wire 326 that results from contracting sleeve 25 is disposed outside of lumen 48 of the sleeve and, therefore, can be cut in order to avoid this loose portion of the wire from moving freely within the heart.

It is to be noted that, unlike for contraction wire 26 of systems 20, 120, and 220, the proximal portion of contraction wire 326 of system 320 serves as a guide member along which the adjustment tool can be advanced toward the implant.

Reference is again made to FIGS. 1A-4D. For some applications of the invention, the locking mechanism of a given system can be replaced with a one-way mechanism such as a ratchet, mutatis mutandis. The one-way mechanism would be coupled to the contraction wire, and to the sleeve at the second sleeve-end-portion, and would be configured to allow one-way movement of the wire through the one-way mechanism. The system would be arranged such that the one-way mechanism (i) allows increasing the longitudinal proportion of the wire that is disposed within the lumen, and (ii) inhibits reducing the longitudinal proportion of the wire that is disposed within the lumen.

Reference is now made to FIGS. 5A-C, which are schematic illustrations of an annuloplasty system 420 for treating native valve 10, in accordance with some applications of the invention. Except where noted, system 420, including its components and implantation, are typically the same as system 20, correspondingly-named components, and its implantation, mutatis mutandis. System 420 comprises an implant 422, which comprises implant body 24 (comprising sleeve 25) and contraction wire 26, e.g., as described hereinabove, mutatis mutandis.

FIG. 5A schematically shows implant 422 following its implantation at valve 10. Implant 422 is shown attached with the tissue-coupling element 34 of each anchor 32 extending through the circumferential wall of sleeve 25 and into the annulus of the valve, but other attachment means (e.g., sutures, clips, etc.) are also possible. For the sake of clarity, the tissue into which tissue-coupling elements 34 penetrates is not shown. First wire-end 52 is typically attached (e.g., fixedly attached) to sleeve 25 at first sleeve-end-portion 42, and wire 26 extends, in association with the circumferential wall of the sleeve, from the first sleeve-end-portion to second sleeve-end-portion 44. In some embodiments, as shown, the association between wire 26 and circumferential wall 46 is provided by the wire being woven along or as part of the circumferential wall between first sleeve-end-portion 42 and second sleeve-end-portion 44.

Implant 422 comprises an adjustment mechanism 480 coupled to implant body 24 (e.g., to sleeve 25), for example at second sleeve-end-portion 44. Wire 26 is arranged with respect to sleeve 25 and adjustment mechanism 480 such that drawing the wire into the adjustment mechanism longitudinally contracts the sleeve (e.g., drawing portions 42 and 44 closer together). For some applications, as shown, adjustment mechanism 480 is disposed outside of lumen 48. For some applications, adjustment mechanism 480 is disposed within lumen 48 or partially within the lumen.

Adjustment mechanism 480 comprises a pulley system 482 and an actuator 486. For some applications, adjustment mechanism 480 further comprises a housing 488 that houses pulley system 482 and/or actuator 486. For applications in which adjustment mechanism 480 comprises housing 488, actuator 486 (e.g., an actuator interface 496 thereof) is typically accessible from outside of the housing. Although adjustment mechanism 480 is shown as being disposed outside of sleeve 25, for some applications the adjustment mechanism is disposed within the lumen of the sleeve.

Pulley system 482 comprises a plurality of pulleys 484 that comprises at least a first pulley 484a and a second pulley 484b. Actuator 486 is typically coupled to pulley system 482 such that actuation of the actuator adjusts a distance between pulleys 484a and 484b. Pulley system 482 is engaged with wire 26 such that increasing the distance between the first and second pulleys draws the wire into adjustment mechanism 480 (e.g., into housing 488 thereof), thereby longitudinally contracting the sleeve. Therefore, in contrast to adjustment mechanism 280, adjustment mechanism 480 is configured to collect wire 26 upon actuation. It is to be noted, however, that although wire 26 is collected within adjustment mechanism 480, the wire is not collected by increasing wrapping of the wire around the pulleys of the adjustment mechanism. FIG. 5C shows the initial position of pulley 484a in phantom, and the adjusted position of 484a in regular lines. The amount that the distance between pulleys 484a and 484b has been increased by actuation of adjustment mechanism 480 is shown as a distance-increase amount d1.

Typically, pulley system 482 and wire 26 mechanically cooperate such that increasing the distance between pulleys 484a and 484b by distance-increase amount d1 draws, into the adjustment mechanism, a portion of the wire that is longer than distance-increase amount d1, thereby typically longitudinally contracting sleeve 25 by a contraction length d2 (shown in FIG. 5C) that is greater than the distance-increase amount. In some embodiments, this is achieved by wire 26 being arranged, within the adjustment mechanism (e.g., within the pulley system, such as between pulleys 484) in a back-and-forth arrangement that multiplies distance-increase amount.

For some applications, pulley system 482 and wire 26 mechanically cooperate such that the portion of the wire that is drawn into adjustment mechanism 480 is at least twice as long (e.g., at least four times as long, such as at least six times as long), e.g., 2-10 times as long as distance-increase amount. For some applications, pulley system 482 and wire 26 mechanically cooperate such that contraction length d2 is at least twice as long (e.g., at least four times as long, such as at least six times as long), e.g., 2-10 times as long as distance-increase amount.

For some applications, pulley system 482 comprises at least 3 pulleys 484, e.g., with at least 3 (such as at least 4) wire-parts of wire 26 arranged in a back-and-forth arrangement. For some applications, pulley system 482 comprises at least 4 pulleys, e.g., with at least 4 (such as at least 5) wire-parts of wire 26 arranged in a back-and-forth arrangement. For some applications, pulley system 482 comprises at least 5 pulleys, e.g., with at least 5 (such as at least 6) wire-parts of wire 26 arranged in a back-and-forth arrangement. FIGS. 5A-C show an embodiment in which pulley system 482 comprising 5 pulleys 484 (labeled 484a-e) with 6 wire-parts of wire 26 arranged in a back-and-forth arrangement. The wire-parts of wire are labeled 26a-f. For this embodiment, distance-increase amount is multiplied about 6 times, as each wire-part is lengthened by the distance-increase amount. That is, the portion of wire that is drawn into adjustment mechanism 480, and/or contraction length d2, is about 6 times as long as distance-increase amount d1.

For some applications, and as shown, pulley system 482 is similar to a block-and-tackle arrangement used for lifting heavy loads, where each pulley 484 is mounted on one or other of two frames 490, such that each frame and the pulley(s) mounted on it collectively define a respective "block" 492. However, for a regular block-and-tackle, the load is typically attached to one of the blocks, and the applied force is input via the "rope"—by pulling the rope in order to move the blocks together, a mechanical advantage is provided, amplifying force by sacrificing distance moved. In contrast, for adjustment mechanism 480, the applied force is input via the blocks—by moving the blocks apart, the amount of wire drawn into the adjustment mechanism is amplified.

For embodiments in which pulleys 484 are mounted on one or other of two frames to define blocks, distance-increase d1, which is generally defined hereinabove as the increase in distance between pulleys, is the same as the increase in distance between the two blocks (or the two frames thereof). In the embodiment shown, pulleys 484a, 484c, and 484e are mounted to a first frame 490a, thereby defining a first block 492a, and pulleys 484b and 484d are mounted to a second frame 490b, thereby defining a second block 492b. Therefore distance-increase d1 may be defined as the increase in distance between pulleys (e.g., pulleys 484a and 484b), the increase in distance between frames 490a and 490b, and/or the increase in distance between blocks 492a and 492b.

Each of pulleys 484 typically comprises a wheel, e.g., that rotates passively in response to wire 26 moving thereover. However, each pulley 484 can comprise a different suitable bearing, including, for example, a smooth curved surface that does not rotate. For example, each bearing can be a fixed pin over which the wire is slidable.

Actuator 486 can be a linear actuator. For some applications, and as per the embodiment shown, actuator 486 comprises a rotational element, and is actuated by application of a rotational force to rotate the rotational element. For example, and as shown, the rotational element can comprise a leadscrew 494, rotation of which moves one of blocks 492 linearly with respect to the other block.

As described hereinabove, pulley system 482 draws in a length of wire 526 that is greater than the distance that the pulleys and/or blocks move apart. Therefore, whereas a regular block- and tackle amplifies force by sacrificing distance, adjustment mechanism 480 (e.g., pulley system 482 thereof) typically amplifies distance by sacrificing force. It is hypothesized by the inventors that it is therefore advantageous to combine pulley system 482 with an actuator that provides a mechanical advantage in order to facilitate application, to the pulley system (e.g., to block 492a thereof) of a force of sufficient magnitude to contract implant 422 and the tissue to which it is anchored. It is hypothesized by the inventors that actuator 486, comprising leadscrew 494, is such an actuator.

Following implantation of implant 422, an adjustment tool (e.g., a contraction tool) 460 is advanced (e.g., trans-luminally) to the implanted implant, where it engages adjustment interface 496 of adjustment mechanism 480 (FIG. 5B). Tool 460 is used to actuate adjustment mechanism 480 via interface 496 (e.g., by inducing rotation of leadscrew 494), thereby causing contraction of implant 422 (FIG. 5C). For applications in which implant 422 comprises an annuloplasty structure implanted at the native valve annulus, this contraction results in reshaping of the native valve annulus.

For some applications, and as shown, in system 420 (i.e., in implant 422), both ends of contraction wire 26 remain fixed in position (e.g., with respect to sleeve 25) irrespective of the adjustment of the implant. For example, first wire-end 52 can be attached (e.g., fixedly attached) to sleeve 25 at first sleeve-end-portion 42, and second wire-end 54 can be attached (e.g., fixedly attached) to a component of adjustment mechanism 480 that does not move with respect to sleeve 25 upon actuation—such as frame 490b (as shown) or housing 488. Optionally, second wire-end can be attached (e.g., fixedly attached) to a component of adjustment mechanism 480 that does move with respect to sleeve 25 upon actuation—such as frame 490a.

Reference is now made to FIGS. 6A-D and 7A-E, which are schematic illustrations of an exemplary annuloplasty system 520 for treating native valve 10. Except where noted, system 520 and its components are typically the same as system 20, including correspondingly-named components and its implantation, mutatis mutandis. System 520 comprises an implant 522, which comprises implant body 24 (comprising sleeve 25) and a contraction wire 526, e.g., as described hereinabove, mutatis mutandis. Contraction wire 526 is similar to contraction wire 26, except that it extends proximally away from sleeve 25, as described in more detail hereinbelow. Implant 522 further comprises a lock 570 coupled to implant body 24 (e.g., to sleeve 25), for example at second sleeve-end-portion 44.

FIGS. 6A-D show lock 570 and its association with wire 526, and FIGS. 7A-E show at least some steps in the use of system 520, in accordance with some applications of the invention. The association between wire 526 and sleeve 25 is such that pulling progressive regions of the wire away from the sleeve via lock 570 progressively longitudinally contracts the sleeve (e.g., drawing portions 42 and 44 closer together). For some applications, and as shown, lock 570 is disposed outside of lumen 48 of sleeve 25. For some applications, adjustment mechanism 480 is disposed within lumen 48 or partially within the lumen.

Figure 7A:
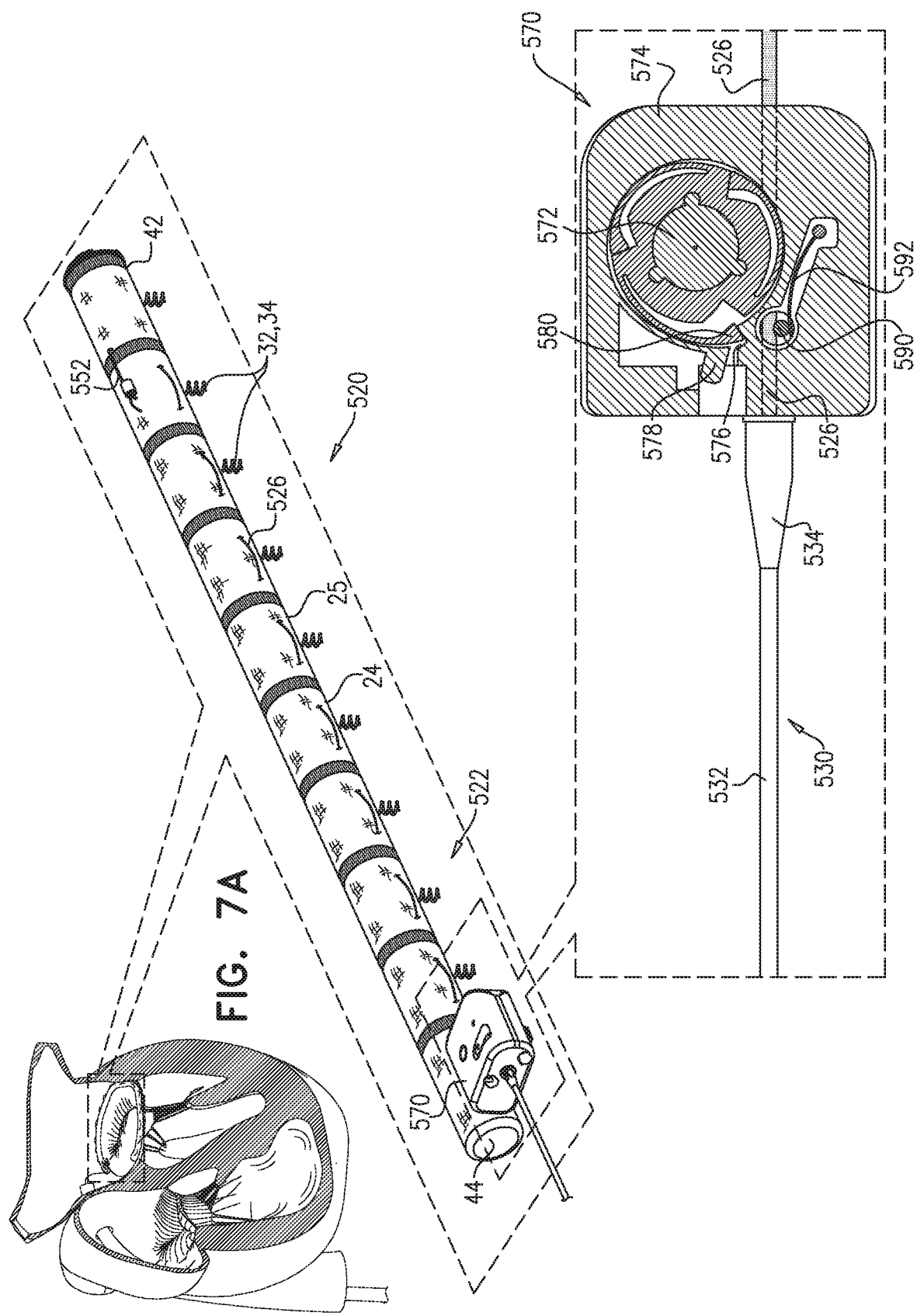

FIG. 7A schematically shows implant 422 following its implantation at valve 10. FIG. 7A depicts implant 422 with the tissue-coupling element 34 of each anchor 32 extending through the circumferential wall of sleeve 25 and into the annulus of the valve, but other attachment means (e.g., sutures, clips, etc.) are also possible. For the sake of clarity, the tissue into which tissue-coupling elements 34 penetrates is not shown. First wire-end 52 is typically attached (e.g., fixedly attached) to sleeve 25 at first sleeve-end-portion 42, and wire 526 extends, in association with the circumferential wall of the sleeve, from the first sleeve-end-portion to second sleeve-end-portion 44. In some embodiments, as shown, the association between wire 26 and circumferential wall 46 is provided by the wire being woven along or as part of the circumferential wall between first sleeve-end-portion 42 and second sleeve-end-portion 44.

Lock 570 comprises a passive capstan 572. Lock 570 can also comprise a housing 574 that houses the capstan, the capstan being rotationally coupled to the housing (e.g., rotationally mounted within the housing). Wire 526 extends (i) from first sleeve-end-portion 42 to second sleeve-end-portion 44 in association with the circumferential wall of sleeve 25, (ii) through lock 570, wrapping at least once around capstan 572, and (iii) away from the lock and the sleeve. As shown in FIG. 7A, implant 522 is implanted in this state, such that wire 526 extends proximally away from the implantation site, typically out of the subject. Typically, wire 526 wraps at least twice around capstan 572. In the example shown, wire 526 wraps three full turns around capstan 572.

Typically, system 520 comprises a guide member 530 that comprises a flexible tube 532. A distal portion 534 of guide member 530 is reversibly coupled to lock 570, and wire 526 extends away from the lock and the sleeve via the tube. This is illustrated, inter alia, in FIGS. 6A and 6D. For some applications, and as shown, the coupling between portion 534 and lock 570 is a screw coupling. Implant 522 can be implanted in this state, e.g., as shown in FIG. 7A.

The wrapping of wire 526 around capstan 572 is such that movement of the wire through lock 570 rotates the capstan. While not wishing to be constrained by a particular theorem, it is hypothesized by the inventors that this is due to belt friction. It is to be noted that the term "passive capstan" (including the specification and the claims) means a capstan that rotates passively in response to movement of wire 526, e.g., as opposed to a capstan that is actively rotated in order to pull the wire.

Lock 570 has discrete unlocked and locked states, and is reversibly switchable between the unlocked state and the locked state. In the unlocked state capstan 572 is rotatable (e.g., with respect to housing 574 and/or with respect to sleeve 25), thereby facilitating movement of the wire through the lock. In the locked state, rotation of capstan 572 is locked in at least one direction, thereby preventing movement of the wire through the lock. Again, while not wishing to be constrained by a particular theorem, it is hypothesized by the inventors that this prevention of movement of the wire is due to belt friction.

Typically, lock 570 is biased toward being in the locked state, though it need not be.

For some applications, and as shown, the rotational locking of capstan 572 is provided by at least one detent 580. For such applications in which lock 570 is biased toward being in the locked state, the at least one detent can be biased to rotationally lock capstan 572 with respect to housing 574.

For some applications, and as shown, the at least one detent 580 is attached to capstan 572, and is configured to rotationally lock the capstan with respect to housing 574 by engaging the housing. For example, housing 574 can be shaped to define a recess 576, and the at least one detent 580 can be configured to engage the housing by protruding into the recess.

Figure 7B:
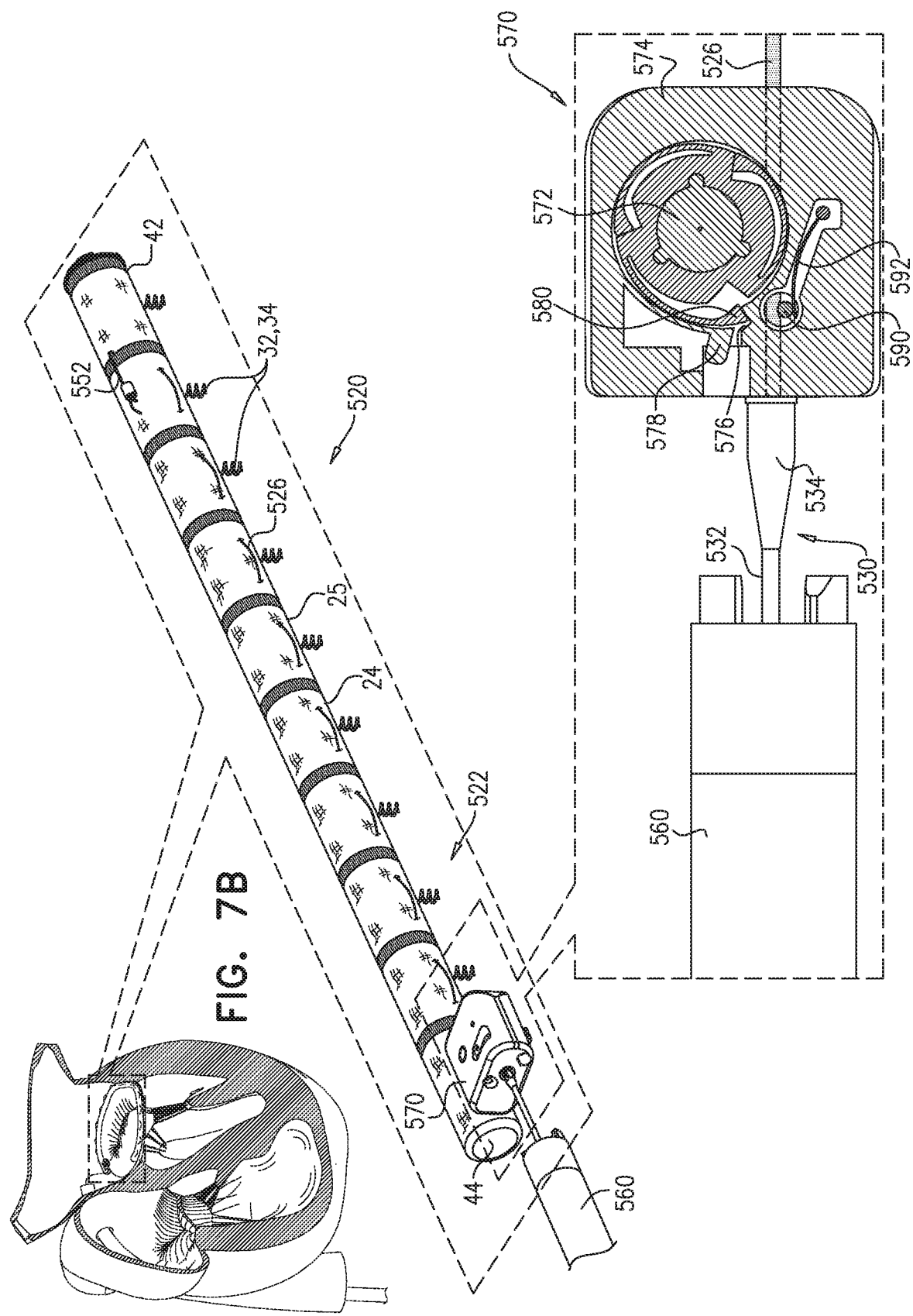

Following implantation of implant 522, an adjustment tool 560 is transluminally advanced to the implant (FIG. 7B). In some embodiments, tool 560 is advanced over and along proximal portions of wire 526. For applications in which system 520 comprises guide member 530, tube 532 is already disposed over wire 526, and tool 560 is advanced over and along tube 532 (as well as over and along wire 526 therewithin).

Tool 560 engages lock 570, and is used to switch the lock into the unlocked state (FIG. 7C). For example, tool 560 may push detent 580 out of recess 576, and/or may obstruct the at least one detent from engaging the recess. For some applications, and as shown, housing 574 comprises a button 578 that, when pressed, switches the lock into the unlocked state by obstructing the detent from engaging the recess. For such applications, tool 560 can press button 578—e.g., as shown.

Subsequently, wire 526 is pulled proximally away from sleeve via the lock, thereby longitudinally contracting implant 522 (FIG. 7D). As shown, detent 580 rotates in response to the movement of wire 526. For some applications, tool 560 (e.g., a proximal portion thereof) is configured to pull wire 526. For some applications, wire 526 is pulled via a different means, e.g., with tool 560 serving merely to unlock lock 570 and to provide a counter-force to facilitate pulling of the wire.

Once a desired degree of contraction is achieved, lock 570 is switched to the locked state (FIG. 7E). For example, for applications in which lock 570 is biased toward being in the locked state, the lock can simply be allowed to automatically return to the locked state—e.g., by releasing button 578. At this stage, tool 560 can be removed from the subject (e.g., as shown in FIG. 7E). Optionally, further adjustment of the contraction of implant 522 can be performed by repeating the previous steps, mutatis mutandis.

In some embodiments, after contraction of implant 522, excess wire 526 is removed. For example, tool 560 can comprise a cutter, or a dedicated cutter can be used—e.g., advanced over and along wire 526 (and/or guide member 530, if guide member 530 is still present).

Typically, after contraction of implant 522, guide member 530 is decoupled (e.g., unscrewed) from lock 570, and removed from the subject. This is illustrated by the absence of the guide member in FIG. 7E. For some applications, guide member 530 is removed simultaneously with tool 560. For some applications, guide member 530 is left in place for at least some time after tool 560 is removed, e.g., to facilitate re-adjustment and/or to facilitate advancement of a cutter for removal of excess wire 526.

For some applications, in the locked state, rotation of the capstan is bidirectionally locked. Optionally, and as shown, in the locked state, rotation of the capstan is unidirectionally locked, e.g., such that wire 526 can pass proximally through lock 570 to contract implant 522, but cannot pass back again. In the unlocked state, capstan 572 can be bidirectionally rotatable.

For some applications, and as shown, lock 570 is configured to be lockable in any of a plurality of rotational positions of capstan 572. Therefore, for some applications, the at least one detent 580 is biased to rotationally lock capstan 572 in a plurality of rotational positions with respect to housing 574. For example, and as shown, lock 570 can comprise a plurality of detents 580, each biased to rotationally lock capstan 572 in a corresponding rotational position with respect to the housing. In the example shown, lock 570 comprises three detents 580 distributed around capstan 572, providing three rotational locking positions at 120-degree intervals.

For some applications, lock 570 further comprises a mechanical resistor 590 that is configured to partially resist movement of the wire through the lock, independent of whether the lock is in the unlocked state or the locked state. It is hypothesized by the inventors that resistor 590 provides greater control over wire 526, e.g., by maintaining tensions of the wire wrapped around the capstan. Resistor 590 can be provided in one of many forms, but in the example shown, the resistor is a bar that is pressed against wire 526 by a spring 592.

It is to be noted that although wire 526 is wrapped around capstan 572, this wrapping is not increased during contraction of sleeve 25. Wire 526 is not collected within lock 570 during contraction of sleeve 25.

It is hypothesized by the inventors that lock 570 provides at least two advantages, e.g., compared to some other locking mechanisms. Firstly, the amount of contact between lock 570 (e.g., capstan 572 thereof) and wire 526 typically remains constant at all times, irrespective of whether lock 570 is in the locked or unlocked state, and irrespective of a degree of contraction of sleeve 25. Therefore the "locking" is, in effect, locking between two components of lock—e.g., as opposed to an induced locking of a component of the lock to the wire. Secondly, lock 570 provides a large amount of contact with wire 526, and therefore the locking force applied by the lock to the wire is spread over a larger surface area of the wire compared to a lock that might contact the wire over a smaller surface area, such as a crimpable bead. It is hypothesized that these features advantageously increase control, reliability, and safety.

Methods involving the systems and devices herein can include any of the steps described above, e.g., to implant, attach, contract, lock, etc. the systems, devices, components, etc. In some embodiments, methods involve transvascularly (e.g., transfemorally, etc.) advancing the system, device, implant, etc. to a target location, such as a heart valve annulus or simulation of a heart valve annulus. The methods involve attaching the system, device, implant, etc. to the target location (e.g., after advancement as described previously). Attaching can involve anchoring, suturing, clipping, and/or using other attachment means to attach the system, device, implant, etc. to the target location. The methods also involve contracting the system, device, implant, etc., which can be done by pulling or otherwise exerting force on a contraction wire (which can be attached, configured, and/or arranged as described in any of the embodiments above) to cause the system, device, implant, etc. to contract (e.g., to a contracted configuration with a smaller length, diameter, and/or radius of curvature). The contracting can be done as described with respect to any of the embodiments above. The methods can also include locking a locking mechanism, lock, locking device, etc. to hold the system, device, implant, etc. in the contracted configuration. The locking mechanism, lock, locking device, etc. can be the same and function and/or be operated in the same way as any of those described above.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. For example, a tool described for use with one of the implants described herein can optionally be used with another of the implants described herein, mutatis mutandis. Similarly, an adjustment mechanism or lock described for use in one of the implants described herein can optionally be used in another of the implants described herein, mutatis mutandis. Further, each of the methods, techniques, steps, etc. described herein can be performed on a living animal or on a non-living cadaver, cadaver heart, simulator, anthropomorphic ghost, etc.

The invention claimed is:

1. An apparatus for use at a heart of a subject, the apparatus comprising an annuloplasty implant that comprises:
    a flexible sleeve having a first sleeve-end-portion, a second sleeve-end-portion, and a circumferential wall that defines a longitudinal lumen between the first and second sleeve-end-portions; and
    an elongate contraction wire having a first wire-end and a second wire-end, the first wire-end being attached to the sleeve at the first sleeve-end-portion, and the wire extending, in association with the circumferential wall, from the first sleeve-end-portion to the second sleeve-end-portion,
wherein the wire is arranged with respect to the sleeve such that increasing a longitudinal proportion of the wire that is disposed within the lumen longitudinally contracts the sleeve.

2. The apparatus according to claim 1, further comprising a plurality of anchors, each anchor of the plurality of anchors being independently advanceable into the lumen, and configured to anchor the sleeve to tissue by being driven through the circumferential wall and into the tissue.

3. The apparatus according to claim 1, wherein the second wire-end is disposed within the lumen, and the wire is arranged with respect to the sleeve such that movement of the second wire-end toward the first sleeve-end-portion increases the longitudinal proportion of the wire that is disposed within the lumen by drawing the wire into the lumen.

4. The apparatus according to claim 1, wherein the wire extends from the first sleeve-end-portion to the second sleeve-end-portion in association with the circumferential wall, by weaving along the circumferential wall between the first sleeve-end-portion and the second sleeve-end-portion.

5. The apparatus according to claim 1, further comprising a one-way mechanism, coupled to the wire, configured to allow one-way movement of the wire through the one-way mechanism, and coupled to the sleeve at the second sleeveend-portion in an arrangement that (i) allows increasing the longitudinal proportion of the wire that is disposed within the lumen, and (ii) inhibits reducing the longitudinal proportion of the wire that is disposed within the lumen.

6. The apparatus according to claim 1, further comprising:
a plurality of anchors, each anchor of the plurality of anchors:
comprising an anchor head and a tissue-engaging element,
being independently advanceable into the lumen, and
being configured to anchor the sleeve to tissue by the tissue-engaging element being driven through the circumferential wall and into the tissue while the anchor head remains in the lumen; and
a contraction tool that comprises a wire-engaging element, wherein the wire-engaging element, subsequently to anchoring of the sleeve using the anchors:
is movable longitudinally into the lumen and through the lumen to the second wire-end,
is reversibly couplable, within the lumen, to the second wire-end, and
while coupled to the second wire-end, is movable longitudinally through the lumen and past the anchor heads toward the first sleeve-end-portion, such that the second wire-end is moved toward the first sleeve-end-portion, thereby drawing the wire into the lumen and longitudinally contracting the sleeve.

7. The apparatus according to claim 1, further comprising a contraction tool that comprises a wire-engaging element, wherein the wire-engaging element:
is movable longitudinally into the lumen and through the lumen to the second wire-end,
is reversibly couplable to the second wire-end, and while coupled to the second wire-end, is movable longitudinally toward the first sleeve-end-portion, such that the second wire-end is moved toward the first sleeve-end-portion, thereby drawing the wire into the lumen and longitudinally contracting the sleeve.

8. The apparatus according to claim 1, further comprising a locking mechanism that has:
an unlocked state in which the locking mechanism allows movement of the wire through the locking mechanism, and increasing of the longitudinal proportion of the wire that is disposed within the lumen, and
a locked state in which the locking mechanism inhibits movement of the wire through the locking mechanism.

9. The apparatus according to claim 8, wherein the locking mechanism is a component of the annuloplasty implant and is coupled to the sleeve, and the annuloplasty implant is transluminally-advanceable to the heart with the locking mechanism coupled to the sleeve.

10. The apparatus according to claim 8, further comprising a contraction tool that comprises a wire-engaging element, wherein
the wire-engaging element:
is movable longitudinally into the lumen and through the lumen to the second wire-end,
is reversibly couplable, within the lumen, to the second wire-end, and
while coupled to the second wire-end, is movable longitudinally toward the first sleeve-end-portion, such that the second wire-end is moved toward the first sleeve-end-portion, thereby drawing the wire into the lumen and longitudinally contracting the sleeve, and
the locking mechanism:
is coupled to the contraction tool, and
is advanceable, using the contraction tool, longitudinally through the lumen toward the second sleeve-end-portion and the wire.

11. The apparatus according to claim 8, further comprising a lock tool that engages the locking mechanism, and is configured to transition the locking mechanism into the locked state.

12. The apparatus according to claim 11, wherein the locking mechanism is biased to assume the locked state, the lock tool is configured to retain the locking mechanism in the unlocked state while the lock tool is engaged with the locking mechanism, and the lock tool is configured to transition the locking mechanism into the locked state by disengaging from the locking mechanism.

13. The apparatus according to claim 1, wherein:
the annuloplasty implant further comprises an adjustment mechanism coupled to the sleeve at the second sleeve-end-portion and coupled to the wire, and
the adjustment mechanism is configured such that actuation of the adjustment mechanism increases the longitudinal proportion of the wire that is disposed within the lumen by feeding the wire into the lumen.

14. The apparatus according to claim 13, wherein the adjustment mechanism comprises a capstan.

15. The apparatus according to claim 13, further comprising a guide tube, extending from the adjustment mechanism into the lumen, the actuation of the adjustment mechanism feeding the wire into the lumen by feeding the wire into the tube.

* * * * *